United States Patent
Fieldhouse et al.

(10) Patent No.: US 11,999,745 B2
(45) Date of Patent: Jun. 4, 2024

(54) PHARMACEUTICAL COMPOUNDS

(71) Applicant: Heptares Therapeutics Limited, Cambridgeshire (GB)

(72) Inventors: Charlotte Fieldhouse, Cambridgeshire (GB); Miles Stuart Congreve, Cambridgeshire (GB)

(73) Assignees: Heptares Therapeutics Limited, Cambridgeshire (GB); Allergan Pharmaceuticals Therapeutics International Limited, Dublin (IE)

( * ) Notice: Subject to any disclaimer, the term of this patent is extended or adjusted under 35 U.S.C. 154(b) by 0 days.

(21) Appl. No.: 17/874,564

(22) Filed: Jul. 27, 2022

(65) Prior Publication Data
US 2022/0380379 A1 Dec. 1, 2022

Related U.S. Application Data

(63) Continuation of application No. PCT/GB2021/053372, filed on Dec. 20, 2021.

(30) Foreign Application Priority Data

Dec. 18, 2020 (GB) .................................. 2020191

(51) Int. Cl.
C07D 487/10 (2006.01)
A61P 25/18 (2006.01)
C07D 271/07 (2006.01)

(52) U.S. Cl.
CPC ............ C07D 487/10 (2013.01); A61P 25/18 (2018.01); C07D 271/07 (2013.01)

(58) Field of Classification Search
CPC .. C07D 487/10; C07D 271/07; C07D 451/02; A61P 25/18; A61P 25/28; A61P 29/00
See application file for complete search history.

(56) References Cited

U.S. PATENT DOCUMENTS

| | | |
|---|---|---|
| 5,446,051 A | 8/1995 | Ornstein |
| 5,852,029 A | 12/1998 | Fisher et al. |
| 5,854,245 A | 12/1998 | Duggan et al. |
| 6,335,341 B1 | 1/2002 | Johnson et al. |
| 6,387,930 B1 | 5/2002 | Baroudy et al. |
| 6,699,880 B1 | 3/2004 | Yamakawa et al. |
| 7,067,507 B2 | 6/2006 | Pulley et al. |
| 7,163,938 B2 | 1/2007 | Herron et al. |
| 7,524,852 B2 | 4/2009 | Arai et al. |
| 7,531,537 B2 | 5/2009 | Kawaguchi et al. |
| 8,119,661 B2 | 2/2012 | Cheng et al. |
| 8,476,289 B2 | 7/2013 | Freyne et al. |
| 9,067,951 B2 | 6/2015 | Ebel et al. |
| 9,187,451 B2 | 11/2015 | Congreve et al. |
| 9,266,857 B2 | 2/2016 | Brown et al. |
| 9,573,929 B2 | 2/2017 | Congreve et al. |
| 9,593,106 B2 | 3/2017 | Livermore et al. |
| 9,669,013 B2 | 6/2017 | Brown et al. |
| 9,670,183 B2 | 6/2017 | Brown et al. |
| 9,758,506 B2 | 9/2017 | Brown et al. |
| 9,907,805 B2 | 3/2018 | Congreve et al. |
| 9,926,297 B2 | 3/2018 | Brown et al. |
| 9,957,257 B2 | 5/2018 | Nirogi et al. |
| 9,975,890 B2 | 5/2018 | Brown et al. |
| 10,030,012 B2 | 7/2018 | Livermore et al. |
| 10,030,035 B2 | 7/2018 | Congreve et al. |

(Continued)

FOREIGN PATENT DOCUMENTS

| | | |
|---|---|---|
| EA | 002393 | 5/2016 |
| EP | 0034415 | 8/1981 |

(Continued)

OTHER PUBLICATIONS

Bakker et al., "First-in-man study to investigate safety, pharmacokinetics and exploratory pharmacodynamics of HTL0018318, a novel M1-receptor partial agonist for the treatment of dementias," British Journal of Clinical Pharmacology, 2021, 87(7):2945-2955.

Bradley et al., "AC-260584, an orally bioavailable M1 muscarinic receptor allosteric agonist, improves cognitive performance in an animal model," Neuropharmacology, 2010, 58(2):365-373.

Broadley et al., "Muscarinic Receptor Agonists and Antagonists," Molecules, 2001, 6:142-193.

Cao et al., "Synthesis and Biological and Characterization of 1-methyl-1,2,5,6-tetrahydropyridy-1,2,5- thiadiazole Derivatives as Muscarinic agonists for treatment of Neurological Disorders," J Med Chem., 2003, 46(20):4273-4286.

(Continued)

*Primary Examiner* — Bahar Craigo
*Assistant Examiner* — Manahil Mirghani Ali Abdalhameed
(74) *Attorney, Agent, or Firm* — Fish & Richardson P.C.

(57) ABSTRACT

This invention relates to compounds that are agonists of the muscarinic $M_1$ and $M_4$ receptor and which are useful in the treatment of diseases mediated by the muscarinic $M_1$ and/or $M_4$ receptors. Also provided are pharmaceutical compositions containing the compounds and the therapeutic uses of the compounds. Compounds provided are of formula (1):

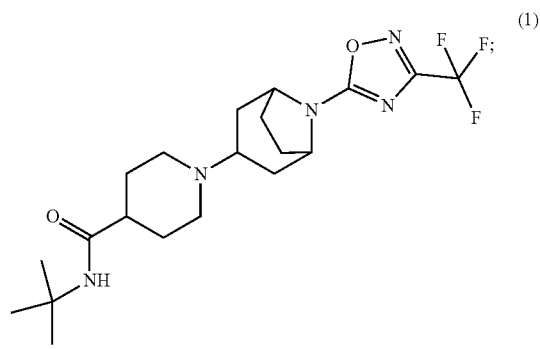

and salts thereof.

31 Claims, 2 Drawing Sheets

(56) References Cited

U.S. PATENT DOCUMENTS

| | | |
|---|---|---|
| 10,167,272 B2 | 1/2019 | Brown et al. |
| 10,167,284 B2 | 1/2019 | Congreve et al. |
| 10,196,380 B2 | 2/2019 | Brown et al. |
| 10,259,787 B2 | 4/2019 | Brown et al. |
| 10,259,802 B2 | 4/2019 | Brown et al. |
| 10,329,278 B2 | 6/2019 | Brown et al. |
| 10,351,545 B2 | 6/2019 | Brown et al. |
| 10,385,039 B2 | 8/2019 | Brown et al. |
| 10,413,553 B2 | 9/2019 | Congreve et al. |
| 10,428,088 B2 | 10/2019 | Congreve et al. |
| 10,501,483 B2 | 12/2019 | Dinh et al. |
| 10,548,884 B2 | 2/2020 | Brown et al. |
| 10,689,368 B2 | 6/2020 | Brown et al. |
| 10,738,029 B2 | 8/2020 | Brown et al. |
| 10,752,610 B2 | 8/2020 | Brown et al. |
| 10,759,751 B2 | 9/2020 | Brown et al. |
| 10,787,447 B2 | 9/2020 | Brown et al. |
| 10,858,352 B2 | 12/2020 | Brown et al. |
| 10,961,225 B2 | 3/2021 | Brown et al. |
| 10,973,832 B2 | 4/2021 | Congreve et al. |
| 11,014,880 B2 | 5/2021 | Brown et al. |
| 11,034,704 B2 | 6/2021 | Congreve et al. |
| 11,091,456 B2 | 8/2021 | Brown et al. |
| 11,208,396 B2 | 12/2021 | Brown et al. |
| 11,254,656 B2 | 2/2022 | Brown et al. |
| 11,319,312 B2 | 5/2022 | Brown et al. |
| 11,324,738 B2 | 5/2022 | Brown et al. |
| 11,352,342 B2 | 6/2022 | Brown et al. |
| 11,773,090 B2 | 10/2023 | Brown et al. |
| 11,834,407 B2 | 12/2023 | Brown et al. |
| 2002/0156081 A1 | 10/2002 | Hirst et al. |
| 2003/0225271 A1 | 12/2003 | Emmanuel et al. |
| 2004/0171614 A1 | 9/2004 | Pissarnitski et al. |
| 2005/0085505 A1 | 4/2005 | Best et al. |
| 2005/0085506 A1 | 4/2005 | Pissarnitski et al. |
| 2005/0176703 A1 | 8/2005 | Gabriel et al. |
| 2006/0194844 A1 | 8/2006 | Sugawawa et al. |
| 2006/0276506 A1 | 12/2006 | Yu et al. |
| 2007/0043023 A1 | 2/2007 | Makings et al. |
| 2007/0054911 A1 | 3/2007 | Drutu et al. |
| 2007/0219218 A1* | 9/2007 | Yu et al. |
| 2008/0015179 A1 | 1/2008 | Makings et al. |
| 2009/0076078 A1 | 3/2009 | Cheng et al. |
| 2013/0012485 A1 | 1/2013 | Baeschlin et al. |
| 2014/0329803 A1 | 11/2014 | Congreve et al. |
| 2015/0232443 A1 | 8/2015 | Brown et al. |
| 2015/0376179 A1 | 12/2015 | Livermore et al. |
| 2016/0068508 A1 | 3/2016 | Congreve et al. |
| 2016/0128996 A1 | 5/2016 | Brown et al. |
| 2017/0015650 A1 | 1/2017 | Brown et al. |
| 2017/0037025 A1 | 2/2017 | Brown et al. |
| 2017/0096437 A1 | 4/2017 | Congreve et al. |
| 2017/0157139 A1 | 6/2017 | Congreve et al. |
| 2017/0183338 A1 | 6/2017 | Livermore et al. |
| 2017/0240530 A1 | 8/2017 | Brown et al. |
| 2017/0247369 A1 | 8/2017 | Brown et al. |
| 2018/0022726 A1 | 1/2018 | Brown et al. |
| 2018/0072727 A1 | 3/2018 | Congreve et al. |
| 2018/0105491 A1 | 4/2018 | Brown et al. |
| 2018/0153900 A1 | 6/2018 | Congreve et al. |
| 2018/0155315 A1 | 6/2018 | Brown et al. |
| 2018/0179184 A1 | 6/2018 | Brown et al. |
| 2018/0222885 A1 | 8/2018 | Brown et al. |
| 2018/0228791 A1 | 8/2018 | Brown et al. |
| 2018/0258085 A1 | 9/2018 | Brown et al. |
| 2018/0327426 A1 | 11/2018 | Congreve et al. |
| 2018/0362507 A1 | 12/2018 | Brown et al. |
| 2019/0112294 A1 | 4/2019 | Brown et al. |
| 2019/0202783 A1 | 7/2019 | Brown et al. |
| 2019/0270718 A1 | 9/2019 | Brown et al. |
| 2019/0276437 A1 | 9/2019 | Brown et al. |
| 2019/0337925 A1 | 11/2019 | Brown et al. |
| 2019/0389849 A1* | 12/2019 | Brown ............... C07D 498/08 |
| 2020/0002328 A1 | 1/2020 | Brown et al. |
| 2020/0017530 A1 | 1/2020 | Congreve et al. |
| 2020/0129496 A1 | 4/2020 | Brown et al. |
| 2020/0165220 A1 | 5/2020 | Brown et al. |
| 2020/0253982 A1 | 8/2020 | Congreve et al. |
| 2020/0290963 A1 | 9/2020 | Brown et al. |
| 2020/0325118 A1 | 10/2020 | Brown et al. |
| 2020/0354339 A1 | 11/2020 | Brown et al. |
| 2021/0002271 A1 | 1/2021 | Brown et al. |
| 2021/0040067 A1 | 2/2021 | Brown et al. |
| 2021/0101893 A1 | 4/2021 | Brown et al. |
| 2021/0353637 A1 | 11/2021 | Congreve et al. |
| 2021/0387969 A1 | 12/2021 | Brown et al. |
| 2022/0017504 A1 | 1/2022 | Brown et al. |
| 2022/0048928 A1 | 2/2022 | Congreve et al. |
| 2022/0213034 A1 | 7/2022 | Brown et al. |
| 2022/0298133 A1 | 9/2022 | Brown et al. |
| 2023/0002354 A1 | 1/2023 | Brown et al. |

FOREIGN PATENT DOCUMENTS

| | | |
|---|---|---|
| EP | 1221443 | 7/2002 |
| EP | 1647553 | 4/2006 |
| EP | 1679069 | 7/2006 |
| EP | 1900732 | 3/2008 |
| JP | S56110674 | 9/1981 |
| JP | H 11-501014 | 1/1999 |
| JP | 2000-501117 | 2/2000 |
| JP | 2000-502360 | 2/2000 |
| JP | 2003-529546 | 10/2003 |
| JP | 2006-509764 | 3/2006 |
| JP | 2006-516145 | 6/2006 |
| JP | 2006-219480 | 8/2006 |
| JP | 2008-521821 | 6/2008 |
| JP | 2009-527569 | 7/2009 |
| JP | 2013-010719 | 1/2013 |
| JP | 2017-505323 | 2/2017 |
| JP | 2018-508562 | 3/2018 |
| RU | 2323218 | 4/2008 |
| RU | 2008130094 | 1/2010 |
| WO | WO 94/15928 | 7/1994 |
| WO | WO 96/13262 | 5/1996 |
| WO | WO 97/16187 | 5/1997 |
| WO | WO 98/57641 | 12/1998 |
| WO | WO 99/32479 | 7/1999 |
| WO | WO 99/32481 | 7/1999 |
| WO | WO 99/32486 | 7/1999 |
| WO | WO 99/32489 | 7/1999 |
| WO | WO 2000/066141 | 11/2000 |
| WO | WO 2000/066559 | 11/2000 |
| WO | WO 2001/027104 | 4/2001 |
| WO | WO 2002/085890 | 10/2002 |
| WO | WO 2003/057672 | 7/2003 |
| WO | WO 2004/014853 | 2/2004 |
| WO | WO 2004/069828 | 8/2004 |
| WO | WO 2004/089942 | 10/2004 |
| WO | WO 2005/037269 | 4/2005 |
| WO | WO 2005/077369 | 8/2005 |
| WO | WO 2006/058294 | 6/2006 |
| WO | WO 2006/068904 | 6/2006 |
| WO | WO 2006/105035 | 10/2006 |
| WO | WO 2007/076070 | 7/2007 |
| WO | WO 2007/079164 | 7/2007 |
| WO | WO 2007/100664 | 9/2007 |
| WO | WO 2007/100670 | 9/2007 |
| WO | WO 2008/021375 | 2/2008 |
| WO | WO 2008/077597 | 7/2008 |
| WO | WO 2008/117229 | 10/2008 |
| WO | WO 2009/034380 | 3/2009 |
| WO | WO 2010/049146 | 5/2010 |
| WO | WO 2010/070032 | 6/2010 |
| WO | WO 2010/121046 | 10/2010 |
| WO | WO 2010/130945 | 11/2010 |
| WO | WO 2011/112825 | 9/2011 |
| WO | WO 2011/133750 | 10/2011 |
| WO | WO 2011/137012 | 11/2011 |
| WO | WO 2011/143057 | 11/2011 |
| WO | WO 2011/150183 | 12/2011 |
| WO | WO 2012/037393 | 3/2012 |
| WO | WO 2012/125661 | 9/2012 |
| WO | WO 2013/072705 | 5/2013 |

(56) References Cited

FOREIGN PATENT DOCUMENTS

| WO | WO 2014/045031 | 3/2014 | | |
|---|---|---|---|---|
| WO | WO 2014/122474 | 8/2014 | | |
| WO | WO 2015/118342 | 8/2015 | | |
| WO | WO 2015/140559 | 9/2015 | | |
| WO | WO 2016/128990 | 8/2016 | | |
| WO | WO 2016/147011 | 9/2016 | | |
| WO | WO 2017/021728 | 2/2017 | | |
| WO | WO 2017/021729 | 2/2017 | | |
| WO | WO 2017/021730 | 2/2017 | | |
| WO | WO 2017/077292 | 5/2017 | | |
| WO | WO2018069732 | * | 4/2018 | ........... C07D 401/08 |
| WO | WO 2018/229511 | 12/2018 | | |
| WO | WO 2019/243850 | 12/2019 | | |
| WO | WO 2019/243851 | 12/2019 | | |
| WO | WO 2020/115505 | 6/2020 | | |
| WO | WO 2020/115506 | 6/2020 | | |
| WO | WO 2022/129951 | 6/2022 | | |
| WO | WO 2022/189366 | 9/2022 | | |

OTHER PUBLICATIONS

Chapman et al., "The muscarinic M4 receptor is the functionally predominant subtype in rat and mouse striatum as demonstrated using [35S] GTPgammaS binding," European Journal of Pharmacology, 2011, 652:1-6.

Chung, "Aberrant phosphorylation in the pathogenesis of Alzheimer's disease," BMB reports, 2009, 42(8):467-474.

Conn et al., "Subtype-selective allosteric modulators of muscarinic receptors for the treatment of CNS disorders," Trends in Pharmacological Sciences, 2009, 30(3):148-155.

Cnn.com [Online], "FDA panel backs late-stage Alzheimer's drug," available on or before Oct. 2, 2003, via Internet Archive: Wayback Machine URL<http://web.archive.org/web/20031002091517/http://www.cnn.com:80/2003/HEALTH/condition s/09/24/alzheimers.drug.ap/index.html>, retrieved on Oct. 21, 22, URL<http://www.cnn.com/2003/HEALTH/conditions/09/24/alzheimers.drug.ap/index.html>, 3 pages.

Fisher, "Cholinergic modulation of amyloid precursor protein processing with emphasis on M 1 muscarinic receptor: perspectives and challenges in treatment of Alzheimer's disease," J Neurochem., 2012, 120(Suppl. 1):22-33.

Foley et al., "The 5-HT(6) receptor antagonist SB-271046 reverses scopolamine-disrupted consolidation of a passive avoidance task and ameliorates spatial task deficits in aged rats," Neuropsychopharmacology, 2004, 29(1):93-100.

Foster et al., "Activation of M1 and M4 muscarinic receptors as potential treatments for Alzheimer's disease and schizophrenia," Neuropsychiatric Disease and Treatment, 2014, 10:183-191.

Gilles et al., "Pharmacological models in Alzheimer's disease research," Dialogues in Clinical Neuroscience, 2000, 2(3):247-255.

Hackam et al., "Translation of research evidence from animals to humans," JAMA, 2006, 296(14):1731-1732.

Hasselmo et al., "Modes and Models of Forebrain Cholinergic Neuromodulation of Cognition," Neuropsychopharmacology Reviews, 2011, 36:52-73.

Jordan, "Tamoxifen: a most unlikely pioneering medicine," Nat Rev Drug Discov., 2003, 2(3):205-213.

Jorden, "World Alzheimer Day: French Doctor Denounces Routine Alzheimer Medications," ZCommunications, retrieved on Dec. 20, 2015, retrieved from URL <https://zcomm.org/znetarticle/world-alzheimer-day-french-doctor-denounces-routine-alzheimer- medications/>, 4 pages.

Katz et al., "Transition from acute to chronic postsurgical pain: risk factors and protective factors," Expert Rev Neurother., May 2009, 9(5): 723-744.

Kuduk et al., "Novel Ml allosteric ligands: a patent review," Expert Opin. Ther. Patents., 2012, 22(12):1385-1398.

Lankin et al., "Protonated 3-fluoropiperidines: an unusual fluoro directing effect and a test for quantitative theories of solvation," J. Am. Chem. Soc., 1993, 115(8):3356-3357.

Lee et al., "Amyloid-beta in Alzheimer disease: the null versus the alternate hypotheses," J Pharmacol. Exp. Ther., Jun. 2007, 321(3):823-829.

Levey, "Muscarine acetylchloline receptor expression in memory circuits: implications for the treatment of Alzheimer disease," PNAS, 1996, 93(24): 13541-13546.

Lima et al., "Bioisosterism: A Useful Strategy for Molecular Modification and Drug Design," Curr Med Chem., 2005, 12:23-49.

Martino et al., "The M1/M4 preferring agonist xanomeline is analgesic in rodent models of chronic inflammatory and neuropathic pain via central site of action, " Pain, 2011, 152:2852-2860.

Meanwell, "Synopsis of Some Recent Tactical Application of Bioisosteres in Drug Design," J Med Chem., 2011, 54(8):2529-2591.

Melancon et al., "Continued optimization of the MLPCN probe ML071 into highly potent agonists of the hMI muscarinic acetylcholine receptor," Bioorg Med Chem Lett., May 15, 2012, 22(10):3467-3472.

Nirogi et al., "Synthesis and SAR of Imidazo[1,5-a]pyridine derivatives as 5-HT4 receptor partial agonists for the treatment of cognitive disorders associated with Alzheimer's disease," European Journal of Medicinal Chemistry, 2015, 103:289-301.

Osatuke et al., "Insight in schizophrenia: a review of etiological models and supporting research," Compr. Psychiatry, Jan-Feb. 2008, 49(1):70-77.

Scarr, "Muscarinic receptors: their roles in disorders of the central nervous system and potential as therapeutic targets," CNS Neuroscience & Therapeutics, 2012, 18:369-379.

Snyder et al., "The Unexpected Diaxial Orientation of cis-3,5-Difluoropiperidine in Water: A Potent CF --- NH Charge-Dipole Effect," J. Am. Chem. Soc., 2000, 122(3):544-545.

Tasker et al., "P110 - Single and Multiple Dose Safety, Tolerability and Pharmacokinetics of the Selective Mi Receptor Partial Agonist HTL0018318 in Healthy Volunteers," The Journal of Prevention of Alzheimer's Disease, 2018, 5(1):S64-S65.

Tasker et al., "Single and multiple dose safety, tolerability and pharmacokinetics of the selective M1 receptor partial agonist HTL0018318 in healthy volunteers," Poster Presentation, Sosei Heptares, Nov. 2018, 2 pages.

Tecle et al., "Design and Synthesis of ml-Selective Muscarinic Agonists: (R)-(-)-(Z)-1- Azabicyclo[2.2.1]heptan-3-one, O-(3-(3'-Methoxyphenyl)-2-propynyl)- oxime Maleate (CI-1017), a Functionally ml-Selective Muscarinic Agonist," J Med Chem., 1998, 41(14):2524-2536.

Tietje et al., "Preclinical Characterization of A-582941: A Novel a7 Neuronal Nicotinic Receptor Agonist with Broad Spectrum Cognition-Enhancing Properties," CNS Neuroscience & Therapeutics, 2008, 14:65-82.

Toja et al., "1-Alkyl-1,2,S,6-tetrahydropyridine-3-carboxaldehyde-0-alkyl-oximes: a new class of potent orally active muscarinic agonists related to arecoline," Eur J Med Chem, 1991, 26:853-868.

Venkatesh et al., "Role of the development scientist in compound lead selection and optimization," J Pharm Sci., 2000, 89:145-154.

Chakraburtty, "Psychotic Disorders: Types of Mental Illnesses," MedicineNet.com, Feb. 1, 2007, 5 pages.

Chen et al., "Animal models of Alzheimer's disease: Applications, evaluation, and perspectives," Zoological Research, 2022, 43(6): 1026-1040.

Confirmatory Assignment Cover Sheet for Application Nos. U.S. Appl. No. 17/024,085; and U.S. Appl. No. 17/024,085, executed on Oct. 10, 2023, recorded on Nov. 3, 2023, 4 pages.

Confirmatory Assignment Cover Sheet for Application Nos. U.S. Appl. No. 18/133,036; U.S. Appl. No. 18/133,036; U.S. Appl. No. 18/133,036; U.S. Appl. No. 18/133,036; and U.S. Appl. No. 18/133,036, executed on Oct. 10, 2023, recorded on Nov. 3, 2023, 4 pages.

Confirmatory Assignment Cover Sheet for U.S. Appl. No. 17/311,121, executed on Oct. 10, 2023, recorded on Nov. 3, 2023, 4 pages.

Confirmatory Assignment Cover Sheet for U.S. Appl. No. 17/874,564, executed on Oct. 10, 2023, recorded on Nov. 3, 2023, 5 pages.

Confirmatory Assignment Cover Sheet for U.S. Appl. No. 18/280,611, executed on Oct. 10, 2023, recorded on Nov. 3, 2023, 4 pages.

Sauerber et al., "Muscarinic cholinergic agonists and antagonists of the 3-(3-alkyl- 1,2,4-oxadiazol-5-y1)-1,2,5,6-tetrahydropyridine type.

(56) References Cited

OTHER PUBLICATIONS

Synthesis and structure-activity relationships, " Journal of Medicinal Chemistry, Feb. 1, 1991, 34(2):687-692.
Showell et al., "Tetrahydropyridyloxadiazoles: semi-rigid muscarinic ligands," Journal of Medicinal Chemitry, Mar. 1, 1991, 34(3): 1086-1094.
Donaghy et al., "The clinical characteristics of dementia with Lewy bodies and a consideration of prodromal diagnosis," Alzheimer's Research & Therapy, 2014, 6:46.

* cited by examiner

PHARMACEUTICAL COMPOUNDS

This invention relates to a class of novel heterocyclic compounds, their salts, pharmaceutical compositions containing them and their use in therapy of the human body. In particular, the invention is directed to a class of compounds, which are agonists of the muscarinic $M_1$ receptor and/or $M_4$ receptor, and hence are useful in the treatment of Alzheimer's disease, schizophrenia, cognitive disorders and other diseases mediated by the muscarinic $M_1/M_4$ receptors, including but not limited to the treatment or alleviation of pain.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 Br J Pharmacol). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 Br J Pharmacology).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al., 1982 Science). In schizophrenia, which is also characterised by cognitive impairments, mAChR density is reduced in the pre-frontal cortex, hippocampus and caudate putamen of schizophrenic subjects (Dean et al., 2002 Mol Psychiatry). Furthermore, in animal models, blockade or lesion of central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting side effects resulting from stimulation of peripheral $M_2$ and $M_3$ mAChRs including disturbed gastrointestinal motility, bradycardia, nausea and vomiting (drugs.com/pro/donepezil; drugs.com/pro/rivastigmine).

Further discovery efforts have targeted the identification of direct $M_1$ mAChR agonists to target increases in cognitive function. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm.

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain sequelae: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, non-amyloidgenic and amyloidogenic. Cleavage of APP by γ-secretase is common to both pathways, but in the former APP is cleaved by an α-secretase to yield soluble APPα. The cleavage site is within the Aβ sequence, thereby precluding its formation. However, in the amyloidgenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3×TgAD transgenic mouse, a model of the different components of Alzheimer's disease (Caccamo et al., 2006 Neuron). Finally, the mAChR agonist cevimeline has been shown to give a small, but significant, reduction in cerebrospinal fluid levels of Aβ in Alzheimer's patients, thus demonstrating potential disease modifying efficacy (Nitsch et al., 2000 Neurol).

Furthermore, preclinical studies have suggested that mAChR agonists display an atypical antipsychotic-like profile in a range of pre-clinical paradigms. The mAChR agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 CNS Drug Rev). Muscarinic receptors have also been implicated in the neurobiology of addiction. The reinforcing effects of cocaine and other addictive substances are mediated by the mesolimbic dopamine system where behavioural and neurochemical studies have shown that the cholinergic muscarinic receptor subtypes play important roles in regulation of dopaminergic neurotransmission. For example M(4) (−/−) mice demonstrated significantly enhanced reward driven behaviour as result of exposure to cocaine (Schmidt et al Psychopharmacology (2011) August; 216(3): 367-78). Furthermore, xanomeline has been demonstrated to block the effects of cocaine in these models.

Muscarinic receptors are also involved in the control of movement and potentially represent novel treatments for movement disorders such as Parkinson's disease, ADHD, Huntingdon's disease, Tourette's syndrome and other syndromes associated with dopaminergic dysfunction as an underlying pathogenetic factor driving disease.

Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 Arch Neural). This compound was also assessed in a small Phase II study of schizophrenics and gave a significant reduction in positive and negative symptoms when compared to placebo control (Shekhar et al., 2008 Am J Psych). However, in all clinical studies xanomeline and other related mAChR agonists have displayed an unacceptable safety margin with respect to cholinergic side effects, including nausea, gastrointestinal pain, diarrhoea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage however management of post-surgical pain is required. Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the $M_1$ receptor in pain is reviewed by D. F. Fiorino and M. Garcia-Guzman, 2012.

More recently, a small number of compounds have been identified which display improved selectivity for the $M_1$ mAChR subtype over the peripherally expressed mAChR subtypes (Bridges et al., 2008 Bioorg Med Chem Lett; Johnson et al., 2010 Bioorg Med Chem Lett; Budzik et al., 2010 ACS Med Chem Lett). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ and/or $M_4$ mAChR over the $M_2$ and $M_3$ receptor subtypes.

THE INVENTION

The present invention provides compounds having activity as muscarinic $M_1$ and/or $M_4$ receptor agonists. More particularly, the invention provides compounds that exhibit selectivity for the $M_1$ and/or $M_4$ receptor relative to the $M_2$ and $M_3$ receptor subtypes.

Accordingly, the invention provides a compound of the formula (1):

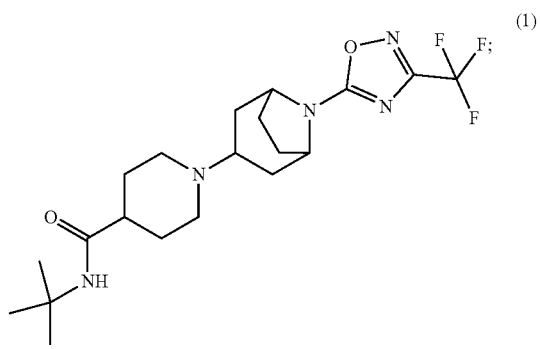 [SMILES: CC(C)(C)NC(=O)C1CCN(C2CC3CCC(C2)N3c2nc(C(F)(F)F)no2)CC1]

or a salt thereof.

The invention further provides a compound of the formula (1a):

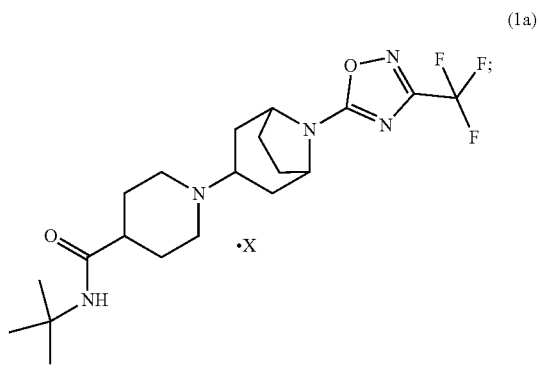

wherein X denotes a salt.

The invention further provides a compound of the formula (1b):

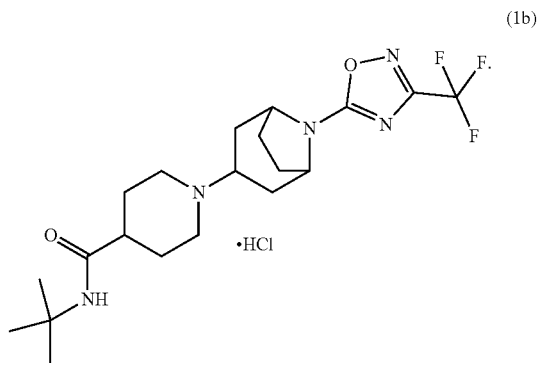 [SMILES: CC(C)(C)NC(=O)C1CCN(C2CC3CCC(C2)N3c2nc(C(F)(F)F)no2)CC1 ; Cl]

The invention further provides a compound of the formula (2):

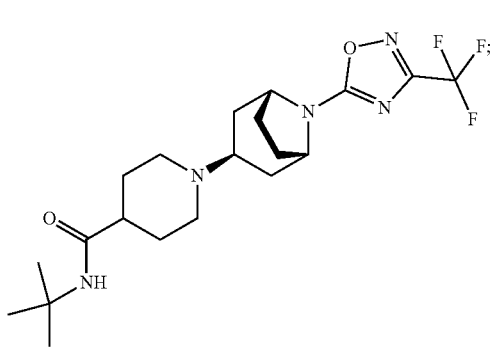

or a salt thereof.

The invention further provides a compound of the formula (2a):

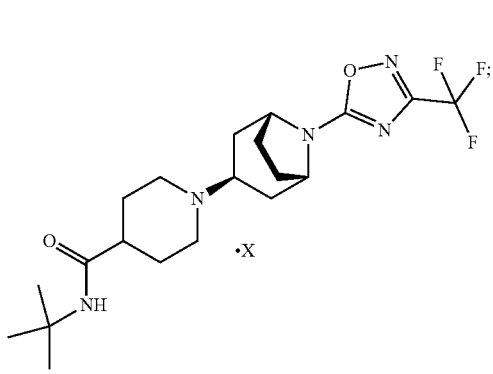

wherein X denotes a salt.

The invention further provides a compound of the formula (2b):

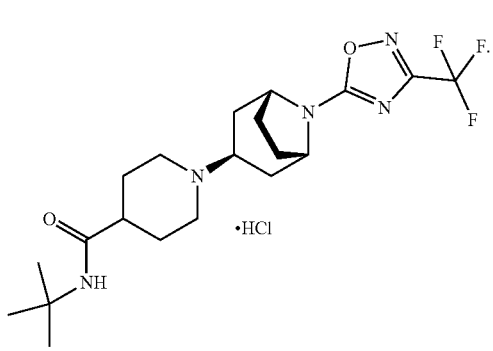

The invention further provides a compound of the formula (2c):

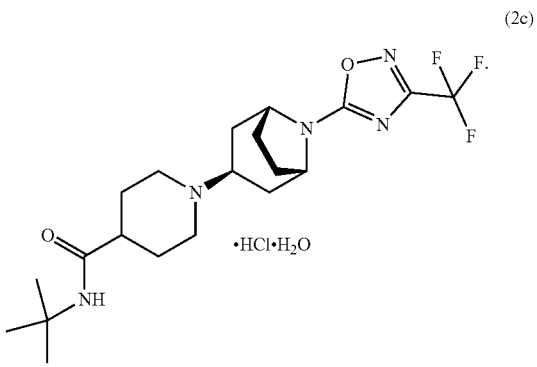

The compound of formula (1) or formula (2) can be a pharmaceutically acceptable salt.

The compound of formula (1) or formula (2) can be an acid addition salt.

The compound of formula (1) or formula (2) can be a hydrochloride salt.

The compound of formula (1) or formula (2) can be a monohydrochloride salt.

The compound of formula (1) or formula (2) can be a monohydrochloride monohydrate salt.

In the compounds of formula (1a) or formula (2a), X can be a pharmaceutically acceptable salt.

In the compounds of formula (1a) or formula (2a), X can be an acid addition salt.

In the compounds of formula (1a) or formula (2a), X can be hydrochloride.

In the compounds of formula (1a) or formula (2a), X can be monohydrochloride.

The compound of formula (1) or formula (2) can be a hydrochloride salt.

X can be hydrochloride. X can be monohydrochloride. X can be monohydrochloride monohydrate.

The compound can be N-tert-butyl-1-{8-[3-(trifluoromethyl)-1,2,4-oxadiazol-5-yl]-8-azabicyclo[3.2.1]octan-3-yl}piperidine-4-carboxamide.

The compound can be N-tert-butyl-1-{(1R,3r,5S)-8-[3-(trifluoromethyl)-1,2,4-oxadiazol-5-yl]-8-azabicyclo[3.2.1]octan-3-yl}piperidine-4-carboxamide.

The compound can be a salt of N-tert-butyl-1-{8-[3-(trifluoromethyl)-1,2,4-oxadiazol-5-yl]-8-azabicyclo[3.2.1]octan-3-yl}piperidine-4-carboxamide.

The compound can be a salt of N-tert-butyl-1-{(1R,3r,5S)-8-[3-(trifluoromethyl)-1,2,4-oxadiazol-5-yl]-8-azabicyclo[3.2.1]octan-3-yl}piperidine-4-carboxamide.

The compound can be a pharmaceutically acceptable salt of N-tert-butyl-1-{8-[3-(trifluoromethyl)-1,2,4-oxadiazol-5-yl]-8-azabicyclo[3.2.1]octan-3-yl}piperidine-4-carboxamide.

The compound can be a pharmaceutically acceptable salt of N-tert-butyl-1-{(1R,3r,5S)-8-[3-(trifluoromethyl)-1,2,4-oxadiazol-5-yl]-8-azabicyclo[3.2.1]octan-3-yl}piperidine-4-carboxamide.

The compound can be N-tert-butyl-1-{8-[3-(trifluoromethyl)-1,2,4-oxadiazol-5-yl]-8-azabicyclo[3.2.1]octan-3-yl}piperidine-4-carboxamide hydrochloride.

The compound can be N-tert-butyl-1-{(1R,3r,5S)-8-[3-(trifluoromethyl)-1,2,4-oxadiazol-5-yl]-8-azabicyclo[3.2.1]octan-3-yl}piperidine-4-carboxamide hydrochloride.

The compound can be N-tert-butyl-1-{8-[3-(trifluoromethyl)-1,2,4-oxadiazol-5-yl]-8-azabicyclo[3.2.1]octan-3-yl}piperidine-4-carboxamide monohydrochloride.

The compound can be N-tert-butyl-1-{(1R,3r,5S)-8-[3-(trifluoromethyl)-1,2,4-oxadiazol-5-yl]-8-azabicyclo[3.2.1]octan-3-yl}piperidine-4-carboxamide monohydrochloride.

The compound can be N-tert-butyl-1-{8-[3-(trifluoromethyl)-1,2,4-oxadiazol-5-yl]-8-azabicyclo[3.2.1]octan-3-yl}piperidine-4-carboxamide monohydrochloride monohydrate.

The compound can be N-tert-butyl-1-{(1R,3r,5S)-8-[3-(trifluoromethyl)-1,2,4-oxadiazol-5-yl]-8-azabicyclo[3.2.1]octan-3-yl}piperidine-4-carboxamide monohydrochloride monohydrate.

Definitions

In this application, the following definitions apply, unless indicated otherwise.

The term "treatment", in relation to the uses of the compounds of the formula (1), formula (1a), formula (1b), formula (2), formula (2a), formula (2b) or formula (2c) is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

Salts

Compounds described herein can exist in the form of salts, for example acid addition salts or, in certain cases salts of organic and inorganic bases such as carboxylate, sulfonate and phosphate salts. All such salts are within the scope of this invention, and references to compounds of the formula (1) and formula (2) include the salt forms of the compounds as defined herein.

The salts are typically acid addition salts.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts may be formed with a wide variety of acids, both inorganic and organic. Examples of acid addition salts falling within the scope of the invention include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

Amine functions in the compounds described herein may form quaternary ammonium salts, for example by reaction with an alkylating agent according to methods well known to the skilled person. Such quaternary ammonium compounds are within the scope of the invention.

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

References to the compounds of formula (1), (1a) and (1b) include all possible stereoisomeric forms thereof (e.g. enantiomers, epimers, and diastereoisomers, including endo-exo isomers), either as individual isomers, or mixtures (e.g. racemic mixtures) or two or more isomers, unless the context requires otherwise.

Accordingly, the invention provides a compound according to formula (1) which contains chiral centres.

The isomers may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415. Stereoisomers can be separated by a number of techniques including chiral chromatography (chromatography on a chiral support) and such techniques are well known to the person skilled in the art. As an alternative to chiral chromatography, stereoisomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more stereoisomeric forms, one diastereomer in a pair of diastereomers may exhibit advantages over the other diastereomer, for example, in terms of biological activity. Thus, in certain circumstances, it may be desirable to use as a therapeutic agent only one of a plurality of diastereoisomers.

Accordingly, the invention provides compositions containing a compound having one or more chiral centres, wherein at least 55% (e.g. at least 60%, 65%, 70%, 75%, 80%, 85%, 90% or 95%) of the compound is present as a single isomer (e.g. diastereoisomer).

In one general embodiment, 99% or more (e.g. substantially all) of the total amount of the compound (or compound for use) is present as a single isomer.

For example, in one embodiment the compound is present as a single diastereomer and the compound has a plane of symmetry.

Isotopes

The compounds of the invention may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise. For example, a reference to an alkyl group such as an tert-butyl group also covers variations in which one or more of the hydrogen atoms in the group is in the form of a deuterium or tritium isotope, e.g. as in a tert-butyl group in which all nine hydrogen atoms are in the deuterium isotopic form (a perdeutero-tert-butyl group).

The isotopes may be radioactive or non-radioactive. The compounds may contain no radioactive isotopes. Such compounds are preferred for therapeutic use. However, the compound may contain one or more radioisotopes. Compounds containing such radioisotopes may be useful in a diagnostic context.

Solvates

Compounds of the invention may form solvates. Preferred solvates are solvates formed by the incorporation into the solid-state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystalising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and dihydrates.

Accordingly, the invention provides:

A compound in the form of a solvate.

A compound wherein the solvate is a hydrate.

A compound wherein the solvate is a monohydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, the invention provides a compound of the invention in an anhydrous form (e.g. anhydrous crystalline form).

Crystalline and Amorphous Forms

The compounds may exist in a crystalline or non-crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra-red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

Accordingly, the invention provides:

A compound in a crystalline form.

A compound which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

A compound which is in an amorphous form.

Complexes and Clathrates

Also encompassed are complexes (e.g. inclusion complexes or clathrates with compounds such as cyclodextrins, or complexes with metals) of the compounds of the invention.

Accordingly, the invention provides a compound in the form of a complex or clathrate.

Biological Activity and Therapeutic Uses

The compounds of the present invention have activity as muscarinic $M_1$ and $M_4$ receptor agonists. The muscarinic activity of the compounds can be determined using the Phospho-ERK1/2 assay described in Example A below.

A significant advantage of compounds of the invention is that they are highly selective for the $M_1$ and $M_4$ receptor relative to the $M_2$ and $M_3$ receptor subtypes. Compounds of the invention are not agonists of the $M_2$ and $M_3$ receptor subtypes. For example, whereas compounds of the invention typically have $pEC_{50}$ values of at least 6 (preferably at least 6.5) and $E_{max}$ values of greater than 80 (preferably greater than 90 against the $M_1$ receptor in the functional assay described in Example A, they may have $pEC_{50}$ values of less than 5 and $E_{max}$ values of less than 20% when tested against the $M_2$ and $M_3$ subtypes in the functional assay of Example A.

With respect the compounds of the invention the invention further provides:

A compound for use in medicine.

A compound for use as a muscarinic $M_1$ and/or $M_4$ receptor agonist.

A compound which is a muscarinic $M_1$ receptor agonist having a $pEC_{50}$ greater than 6.9 and an $E_{max}$ of at least 80 against the $M_1$ receptor in the assay of Example A herein or an assay substantially similar thereto.

A compound which is a muscarinic $M_1$ receptor agonist having a $pEC_{50}$ greater than 7.0.

A compound having an $E_{max}$ of at least 90 against the $M_1$ receptor.

A compound which is a muscarinic $M_1$ and $M_4$ receptor agonist having a $pEC_{50}$ greater than 6.0 against the $M_4$ receptor in the assay of Example A herein or an assay substantially similar thereto.

A compound which is selective for the $M_1$ and $M_4$ receptor compared to the muscarinic $M_2$ and $M_3$ receptors.

A compound which has a $pEC_{50}$ of less than 5 and an $E_{max}$ of less than 30 against the muscarinic $M_2$ and $M_3$ receptor subtypes.

A compound for use in the treatment of a disease or condition mediated by the muscarinic $M_1$ and/or $M_4$ receptor.

By virtue of their muscarinic $M_1$ and $M_4$ receptor agonist activity, compounds of the invention can be used in the treatment of Alzheimer's disease, dementia with Lewy bodies schizophrenia and other psychotic disorders, cognitive disorders and other diseases mediated by the muscarinic $M_1$ and/or $M_4$ receptor, and can also be used in the treatment of various types of pain.

Accordingly, with respect the compounds of the invention the invention further provides:

A compound for use in the treatment of a cognitive disorder or psychotic disorder.

A compound for use in the treatment of a cognitive disorder or psychotic disorder, wherein the cognitive disorder or psychotic disorder comprises, arises from or is associated with a condition selected from cognitive impairment, Mild Cognitive Impairment (MCI), (including amnestic MCI and nonamnestic MCI, and including mild cognitive impairment due to Alzheimer's disease and/or prodromal Alzheimer's disease), frontotemporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease (including prodromal Alzheimer's disease and stages 1, 2, and 3 early Alzheimer's disease as defined by the US Food and Drug Administration's "Early Alzheimer's disease: Developing Drugs for Treatment" available at fda.gov/downloads/Drugs/GuidanceCompli-anceRegulatorylnformation/Guidances/UCM5967 28.pdf), progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, AIDS-related dementia or other dementia states such as multi-infarct dementia, alcoholic dementia, hypothyroidism-related dementia, and dementia associated to other degenerative disorders such as cerebellar atrophy and amyotrophic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, cannabis, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders and schizo-affective disorder.

A compound for use in the treatment of Alzheimer's disease.

A compound for use in the treatment of dementia with Lewy bodies.

A compound for use in the treatment of Schizophrenia.

A method of treatment of a cognitive disorder in a subject (e.g. a mammalian patient such as a human, e.g. a human in need of such treatment), which method comprises the administration of a therapeutically effective dose of a compound of the invention.

A method of treatment of a cognitive disorder in a subject (e.g. a mammalian patient such as a human, e.g. a human in need of such treatment), which method comprises the administration of a therapeutically effective dose of a compound of the invention, wherein the cognitive disorder comprises, arises from or is associated with a condition as defined in above.

A method of treatment of a cognitive disorder in a subject (e.g. a mammalian patient such as a human, e.g. a human in need of such treatment), which method comprises the administration of a therapeutically effective dose of a compound of the invention, wherein the cognitive disorder arises from or is associated with Alzheimer's disease.

A method of treatment of a cognitive disorder in a subject (e.g. a mammalian patient such as a human, e.g. a human in need of such treatment), which method comprises the administration of a therapeutically effective dose of a compound of the invention, wherein the cognitive disorder is dementia with Lewy bodies.

A method of treatment of a cognitive disorder in a subject (e.g. a mammalian patient such as a human, e.g. a human in need of such treatment), which method comprises the administration of a therapeutically effective dose of a compound of the invention, wherein the cognitive disorder is Schizophrenia.

The use of a compound of the invention for the manufacture of a medicament for the treatment of a cognitive disorder.

The use of a compound of the invention for the manufacture of a medicament for the treatment of a cognitive disorder, wherein the cognitive disorder comprises, arises from or is associated with a condition as defined in above.

The use of a compound of the invention for the manufacture of a medicament for the treatment of a cognitive disorder, wherein the cognitive disorder comprises, arises from or is associated with Alzheimer's disease.

The use of a compound of the invention for the manufacture of a medicament for the treatment of a cognitive disorder, wherein the cognitive disorder comprises, arises from or is associated with dementia with Lewy bodies.

The use of a compound of the invention for the manufacture of a medicament for the treatment of a cognitive disorder, wherein the cognitive disorder comprises, arises from or is associated with Schizophrenia.

A compound for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain.

A method of treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain, which method comprises the administration of a therapeutically effective dose of a compound of the invention.

A compound for the treatment of peripheral disorders such as reduction of intra ocular pressure in Glaucoma and treatment of dry eyes and dry mouth including Sjogren's Syndrome.

A method of treatment of peripheral disorders such as reduction of intra ocular pressure in Glaucoma and treatment of dry eyes and dry mouth including Sjogren's Syndrome, which method comprises the administration of a therapeutically effective dose of a compound of the invention.

The use of a compound of the invention for the manufacture of a medicament for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain or for the treatment of peripheral disorders such as reduction of intra ocular pressure in Glaucoma and treatment of dry eyes and dry mouth including Sjogren's Syndrome.

The use of a compound of the invention for the treatment of skin lesions for example due to pemphigus vulgaris, dermatitis herpetiformis, pemphigoid and other blistering skin conditions.

The use of a compound of the invention for treating, preventing, ameliorating or reversing conditions associated with altered gastro-intestinal function and motility such as functional dyspepsia, irritable bowel syndrome, gastroesophageal acid reflux (GER) and esophageal dysmotility, symptoms of gastroparesis and chronic diarrhoea.

The use of a compound of the invention for the treatment of olfactory dysfunction such as Bosma-Henkin-Christiansen syndrome, chemical poisoning (e.g. selenium and silver), hypopituitarism, Kallmann Syndrome, skull fractures, tumour therapy and underactive thyroid gland.

The use of a compound of the invention for the treatment of addiction.

The use of a compound of the invention for the treatment of movement disorders such as Parkinson's disease, ADHD, Huntingdon's disease, Tourette's syndrome and other syndromes associated with dopaminergic dysfunction as an underlying pathogenetic factor driving disease.

The use of a compound of the invention for the treatment of behavioural and psychological symptoms of dementia (BPSD; including agitation, verbal aggressiveness, physical aggressiveness, depression, anxiety, abnormal motor behaviour, elated mood, irritability, apathy, disinhibition, impulsivity, delusions, hallucinations, sleep changes, and appetite changes).

Compounds of the invention include Example 1, Example 1-1 and Example 1-2 shown below.

Example 1

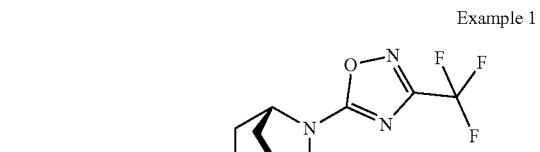

Example 1-1

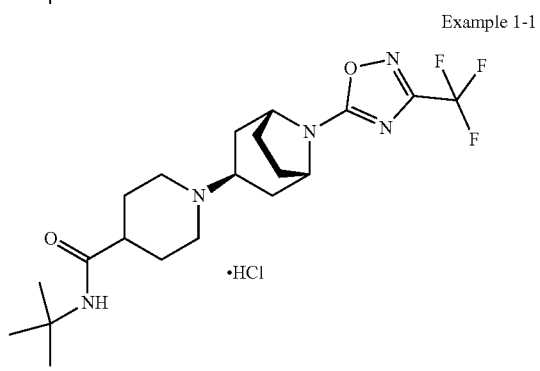

·HCl

Example 1-2

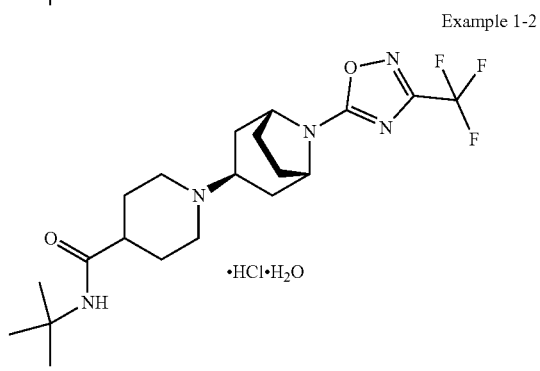

·HCl·H$_2$O

Methods for the Preparation of Compounds of the Invention

Compounds of the invention can be prepared in accordance with synthetic methods well known to the skilled person and as described herein.

Also provided is a process for the preparation of a compound as defined above, which process may comprise any one of A, B or C:

(A) the reaction of a compound of the formula (10):

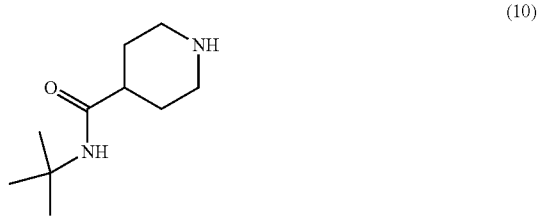

(10)

with a compound of the formula (11):

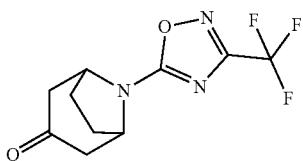

(11)

under reductive amination conditions; or
(B) the reaction of a compound of the formula (12):

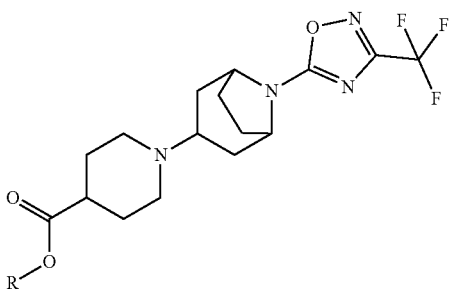

(12)

with an amine of the formula $(CH_3)_3CNH_2$, wherein R represents a suitable group such as methyl or ethyl; or
(C) the reaction of a compound of the formula (13):

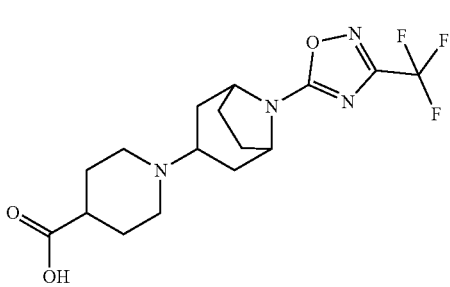

(13)

with an amine of the formula $(CH_3)_3CNH_2$.

Such methods are well known to the skilled person. Examples of synthetic procedures for converting one functional group into another functional group are set out in standard texts such as *March's Advanced Organic Chemistry: Reactions, Mechanisms, and Structure*, 7th Edition, Michael B. Smith, John Wiley, 2013, (ISBN: 978-O-470-46259-1), *Organic Syntheses*, Online Edition, orgsyn.org, (ISSN 2333-3553) and *Fiesers' Reagents for Organic Synthesis*, Volumes 1-17, John Wiley, edited by Mary Fieser (ISBN: 0-471-58283-2).

In the reactions described above, it may be necessary to protect one or more groups to prevent reaction from taking place at an undesirable location on the molecule. Examples of protecting groups, and methods of protecting and deprotecting functional groups, can be found in *Greene's Protective Groups in Organic Synthesis*, Fifth Edition, Editor: Peter G. M. Wuts, John Wiley, 2014, (ISBN: 9781118057483).

Compounds made by the foregoing methods may be isolated and purified by any of a variety of methods well known to those skilled in the art and examples of such methods include recrystallisation and chromatographic techniques such as column chromatography (e.g. flash chromatography), HPLC and SFC.

Pharmaceutical Formulations

While it is possible for the active compound to be administered alone, it is preferable to present it as a pharmaceutical composition (e.g. formulation).

Accordingly, there is provided a pharmaceutical composition comprising at least one compound of the invention as defined above together with at least one pharmaceutically acceptable excipient.

The composition may be a tablet composition.

The composition may be a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the invention can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, optic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, e.g.; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the invention will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

General Procedures

Where no preparative routes are included, the relevant intermediate is commercially available. Commercial reagents were utilised without further purification. Room temperature (rt) refers to approximately 22-30° C. $^1$H NMR spectra were recorded at 400 MHz on a Bruker instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks.

LCMS Analysis

LCMS analysis of compounds was performed under electrospray conditions using the instruments and methods given in the tables below:

| System | Instrument Name | LC Detector | Mass Detector |
|---|---|---|---|
| 1 | Agilent 1290 RRLC | Diode Array Detector | Agilent 6120 MS-2020 |
| 2 | Shimadzu Nexera | Photo Diode Array | |

| Method Name | Solvent System | Column used | Gradient (Solvent A:B) | UV Range | Mass Range | Column Temp. ° C. | Flow Rate mL/min |
|---|---|---|---|---|---|---|---|
| A | (A) 5 mM ammonium acetate & 0.1% formic acid in water (B) 0.1% formic acid in acetonitrile | BEH C-18 2.1 × 50 mm, 1.7 μm or equivalent | 98:2 at 0.01 min, 10:90 at 5.00 min, 5:95 at 6.00 min up to 7.00 min, 98:2 at 7.01 min up to 8.00 min | 200-400 nm | 60-1000 amu | Ambient | 0.45 |
| B | (A) 0.1% ammonia in water (B) 0.1% ammonia in acetonitrile | X-BRIDGE C-18 50 × 4.6 mm, 3.5 μm or equivalent | 95:5 at 0.01 min, 5:95 at 5.80 min up to 7.20 min, 95:5 at 7.21 min up to 10.00 min | 200-400 nm | 60-1000 amu | Ambient | 1.00 |

Preparative HPLC Purification

Preparative HPLC purification was performed using Shimadzu LC-20AP binary system with SPD-20A UV detector. Purification technique: [phase (column description, column length×internal diameter, particle size), solvent flow-rate, gradient–given as % of mobile phase B in mobile phase A (over time), mobile phase (A), mobile phase (B)].

Preparative HPLC Method A

Prep HPLC: [Reversed Phase (X-BRIDGE C-18, 250×50 mm, 5 μm), 85 mL/min, gradient 35%-70% (over 26 min), 100% (over 2 min), 100%-35% (over 6 min), mobile phase (A): 5 mM ammonium bicarbonate in water+0.1% ammonia in water, (B): 100% acetonitrile].

Preparative HPLC Method B

Prep HPLC: [Reversed Phase (X-BRIDGE C-18, 250×50 mm, 5 μm), 85 mL/min, gradient 40%-60% (over 26 min), 60% (over 4 min), 100% (over 2 min), 100%-40% (over 7 min), mobile phase (A): 5 mM ammonium bicarbonate in water+0.1% ammonia in water, (B): 100% acetonitrile].

ABBREVIATIONS

AcOH=acetic acid
Bn=benzyl
t-BuOH=tert-butyl alcohol
CPM=cyclopentyl methyl ether
DCM=dichloromethane
DIPEA=N, N-diisopropylethylamine
DMF=dimethylformamide
DMSO=dimethyl sulfoxide
ESI=electrospray ionization
EtOH=ethanol
h=hour/s
HATU=hexafluorophosphate azabenzotriazole tetramethyl uronium
HPLC=high performance liquid chromatography
IPA=propan-2-ol
LCMS=liquid chromatography mass spectrometry
MeOH=methanol
min=minute/s
2-MTHF=2-methyltetrahydrofuran
nm=nanometre(s)
NMO=4-methylmorpholine 4-oxide
NMR=nuclear magnetic resonance
rt=room temperature
RT=retention time
TEA=triethylamine
TFA=trifluoroacetic acid
TFAA=trifluoroacetic anhydride
THF=tetrahydrofuran Prefixes n-, s-, i-, t- and tert- have their usual meanings: normal, secondary, iso, and tertiary.

Synthesis of N-(tert-butyl)-1-((1R,3r5S)-8-(3-(trifluoromethyl)-1,2,4-oxadiazol-5-yl)-8-azabicyclo[3.2.1]octan-3-yl)piperidine-4-carboxamide hydrochloride (Example 1-1)

Example 1-1

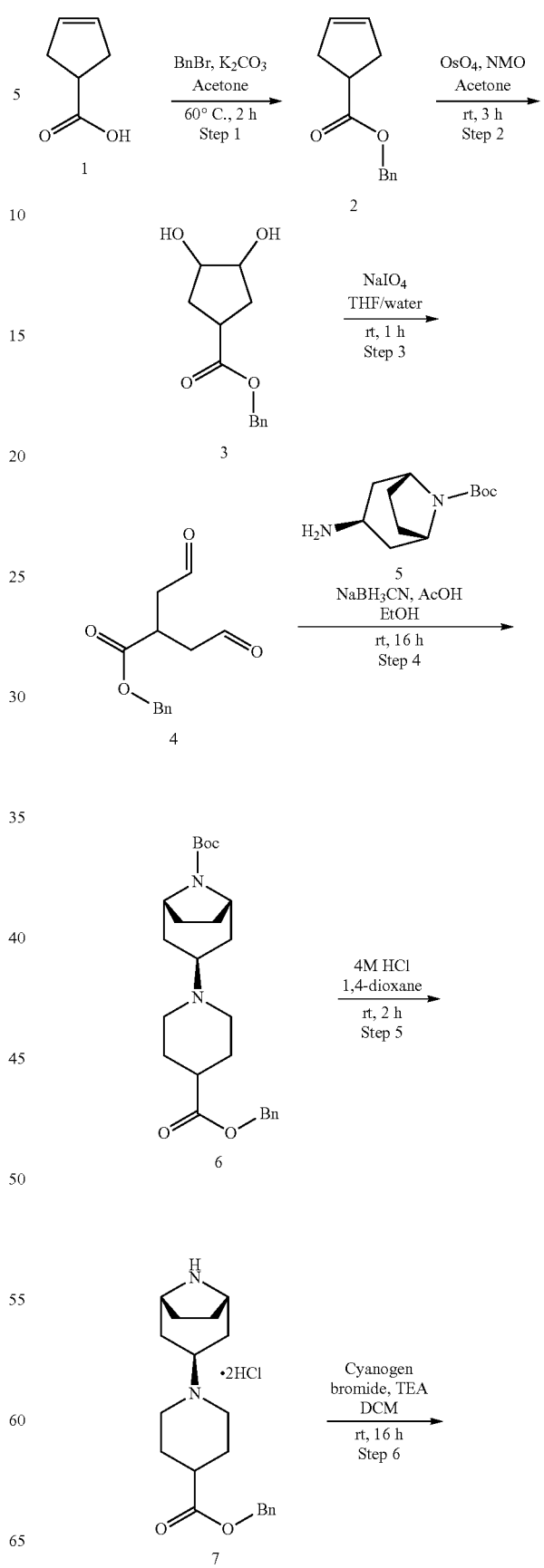

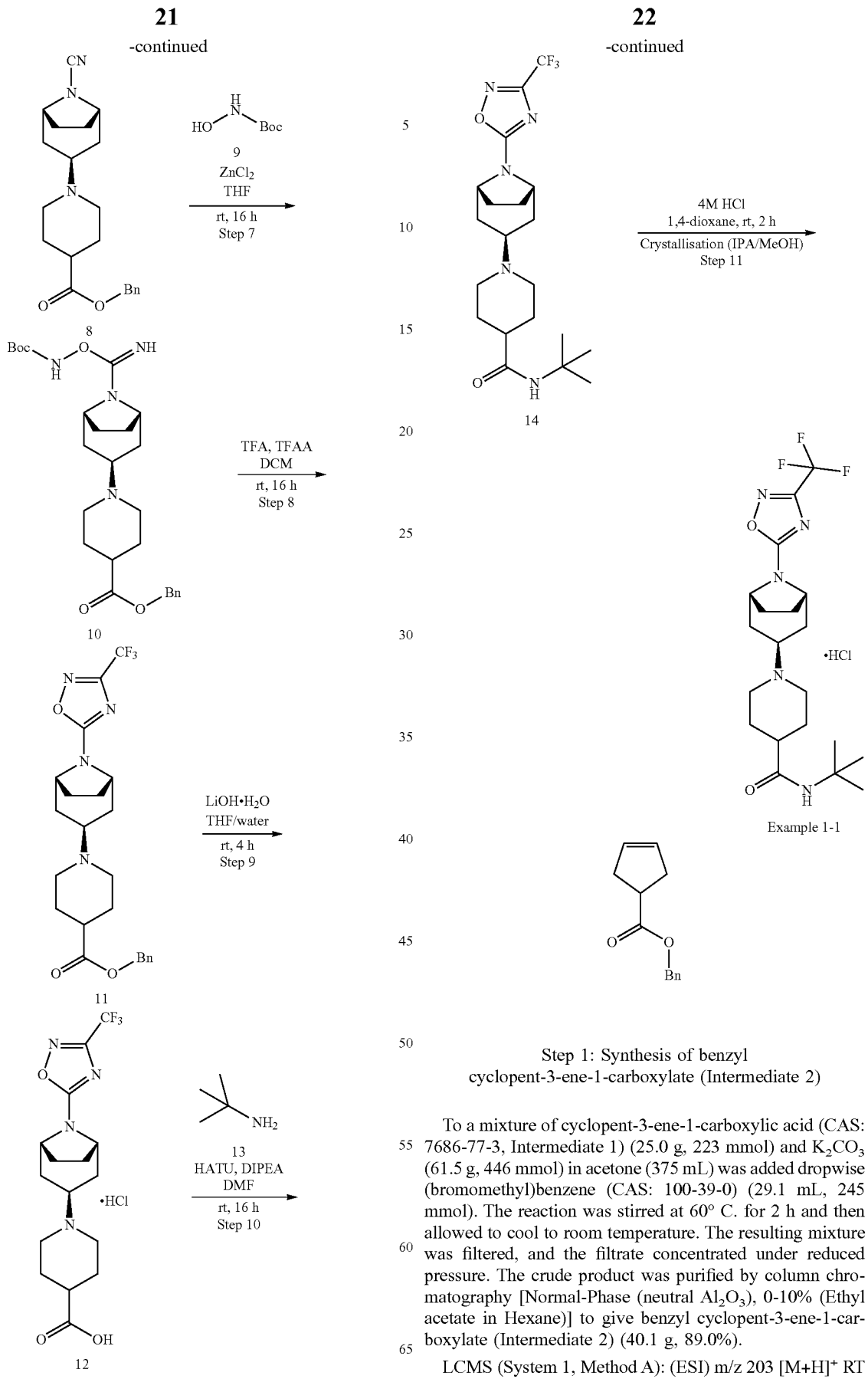

Step 1: Synthesis of benzyl cyclopent-3-ene-1-carboxylate (Intermediate 2)

To a mixture of cyclopent-3-ene-1-carboxylic acid (CAS: 7686-77-3, Intermediate 1) (25.0 g, 223 mmol) and K$_2$CO$_3$ (61.5 g, 446 mmol) in acetone (375 mL) was added dropwise (bromomethyl)benzene (CAS: 100-39-0) (29.1 mL, 245 mmol). The reaction was stirred at 60° C. for 2 h and then allowed to cool to room temperature. The resulting mixture was filtered, and the filtrate concentrated under reduced pressure. The crude product was purified by column chromatography [Normal-Phase (neutral Al$_2$O$_3$), 0-10% (Ethyl acetate in Hexane)] to give benzyl cyclopent-3-ene-1-carboxylate (Intermediate 2) (40.1 g, 89.0%).

LCMS (System 1, Method A): (ESI) m/z 203 [M+H]$^+$ RT 5.10 min, 254 nm.

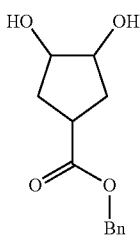

Step 2: Synthesis of benzyl 3,4-dihydroxycyclopentane-1-carboxylate (Intermediate 3)

A mixture of benzyl cyclopent-3-ene-1-carboxylate (Intermediate 2) (43.8 g, 217 mmol), OsO4 (2% in t-BuOH, 12.0 mL, 0.94 mmol) and 4-methylmorpholine 4-oxide (30.44 g, 260 mmol) in acetone (431 mL) was stirred at room temperature for 16 h. The mixture was treated with saturated aqueous $Na_2SO_3$ solution (500 mL) and then extracted with DCM (3×400 mL). The combined organic layers were dried ($Na_2SO_4$) and concentrated under reduced pressure. The resulting residue was purified by column chromatography [Normal-Phase (silica), 0-50% (Ethyl acetate in Hexane)] to give benzyl 3,4-dihydroxycyclopentane-1-carboxylate (Intermediate 3) (30.4 g, 59.4%).

LCMS (System 2, Method B): (ESI) m/z 237 [M+H]+ RT 2.38 min, 224 nm.

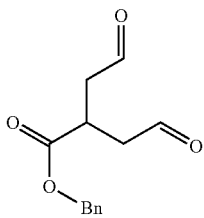 [SMILES: O=CCC(CC=O)C(=O)OCc1ccccc1]

Step 3: Synthesis of benzyl 4-oxo-2-(2-oxoethyl)butanoate (Intermediate 4)

A mixture of benzyl 3,4-dihydroxycyclopentane-1-carboxylate (Intermediate 3) (36.0 g, 153 mmol) and NaIO4 (48.7 g, 229 mmol) in THF (1800 mL) and water (144 mL) was stirred at room temperature for 2 h. Water (1500 mL) was added until the precipitate dissolved and the mixture was then extracted with DCM (3×500 mL). The combined organic layers were dried ($Na_2SO_4$) and concentrated under reduced pressure to give benzyl 4-oxo-2-(2-oxoethyl)butanoate (Intermediate 4) (35.8 g, 100.0%). The crude product was used without further purification.

LCMS (System 2, Method B): (ESI) m/z 233 [M−H]− RT 2.33 min and 2.74 min, 202 nm.

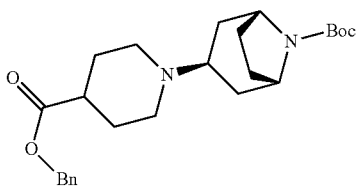 [SMILES: CC(C)(C)OC(=O)N1[C@@H]2CC[C@H]1C[C@@H](N1CCC(C(=O)OCc3ccccc3)CC1)C2]

Step 4: Synthesis of tert-butyl (1R,3r,5S)-3-(4-((benzyloxy)carbonyl)piperidin-1-yl)-8-azabicyclo[3.2.1]octane-8-carboxylate (Intermediate 6)

A solution of tert-butyl (1R,3r,5S)-3-amino-8-azabicyclo[3.2.1]octane-8-carboxylate (CAS: 207405-68-3, Intermediate 5) (34.6 g, 153 mmol) and benzyl 4-oxo-2-(2-oxoethyl)butanoate (Intermediate 4) (35.8 g, 153 mmol) in EtOH (1400 mL) was stirred at room temperature for 30 min. To this was then added NaBH3CN (9.64 g, 153 mmol) and AcOH (3.0 mL, 52.5 mmol) and stirring was continued at room temperature for 16 h. The reaction mixture was diluted with water (1000 mL) and extracted with DCM (3×500 mL). The combined organic layers were dried ($Na_2SO_4$) and concentrated under reduced pressure. The resulting residue was purified by column chromatography [Normal-Phase (silica), 0-30% (Ethyl acetate in Hexane)] to give tert-butyl (1R,3r,5S)-3-(4-((benzyloxy)carbonyl)piperidin-1-yl)-8-azabicyclo[3.2.1]octane-8-carboxylate (Intermediate 6) (41.0 g, 62.6%).

LCMS (System 2, Method B): (ESI) m/z 429 [M+H]+ RT 4.28 min, 202 nm.

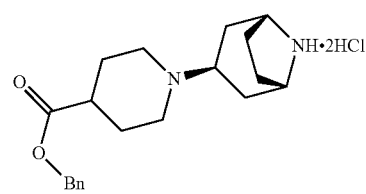

Step 5: Synthesis of benzyl 1-((1R,3r5S)-8-azabicyclo[3.2.1]octan-3-yl)piperidine-4-carboxylate dihydrochloride (Intermediate 7)

To a solution of tert-butyl (1R,3r,5S)-3-(4-((benzyloxy)carbonyl)piperidin-1-yl) azabicyclo[3.2.1]octane-8-carboxylate (Intermediate 6) (41.0 g, 96.0 mmol) in 1,4-dioxane (82.0 mL) at 0° C. was added dropwise HCl in 1,4-dioxane (4M, 410 mL, 10 vol). The reaction mixture was stirred at room temperature for 2 h and then concentrated under reduced pressure. The resulting residue was azeotroped with hexane (2×50 mL) and then triturated with hexane (2×50 mL) to give benzyl 1-((1R,3r,5S)-8-azabicyclo[3.2.1]octan yl)piperidine-4-carboxylate dihydrochloride (Intermediate 7) (38.4 g, 100.0%). LCMS (System 1, Method B): (ESI) m/z 329 [M+H]+ RT 3.10 min, 202 nm.

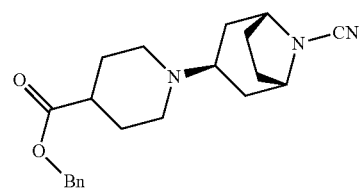 [SMILES: N#CN1[C@@H]2CC[C@H]1C[C@@H](N1CCC(C(=O)OCc3ccccc3)CC1)C2]

Step 6: Synthesis of benzyl 1-((1R,3r5S)-8-cyano-8-azabicyclo[3.2.1]octan-3-yl)piperidine-4-carboxylate (Intermediate 8)

To a solution of benzyl 1-((1R, 3r,5S)-8-azabicyclo[3.2.1]octan-3-yl)piperidine-4-carboxylate dihydrochloride (Intermediate 7) (38.4 g, 96.0 mmol) in DCM (314 mL) at −20° C. was added dropwise triethylamine (39.8 mL, 287 mmol), maintaining an internal temperature in the range of −20° C. to 0° C. The reaction was then stirred at this temperature for 30 min. To this was then added dropwise cyanogen bromide (15.1 g, 144 mmol) as a solution in DCM (31.0 mL), maintaining an internal temperature in the range of −20° C. to 0° C. This was then allowed to warm to room temperature and stirred for 16 h. The reaction mixture was diluted with saturated aqueous NaHCO$_3$ solution (700 mL) and extracted with DCM (3×300 mL). The combined organic layers were dried (Na$_2$SO$_4$) and concentrated under reduced pressure. The crude product was purified by column chromatography [Normal-Phase (neutral Al$_2$O$_3$), 0-30% (Ethyl acetate in Hexane)] to give benzyl 1-((1R,3r,5S)-8-cyano-8-azabicyclo[3.2.1]octan-3-yl)piperidine-4-carboxylate (Intermediate 8) (16.0 g, 47.4%).

LCMS (System 2, Method B): (ESI) m/z 354 [M+H]$^+$ RT 3.69 min, 202 nm.

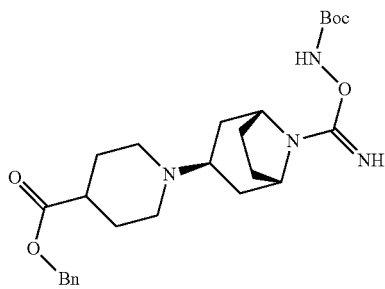 [SMILES: CC(C)(C)OC(=O)NOC(=N)N1[C@@H]2CC[C@H]1C[C@@H](N1CCC(C(=O)OCc3ccccc3)CC1)C2]

Step 7: Synthesis of benzyl 1-((1R,3r5S)-8-((((tert-butoxycarbonyl)amino)oxy)(imino)methyl)-8-azabicyclo[3.2.1]octan-3-yl)piperidine-4-carboxylate (Intermediate 10)

To a solution of benzyl 1-((1R,3r,5S)-8-cyano-8-azabicyclo[3.2.1]octan-3-yl)piperidine carboxylate (Intermediate 8) (16.0 g, 45.3 mmol) in THF (160 mL) at 0° C. was added tert-butyl hydroxycarbamate (CAS: 36016-38-3, Intermediate 9) (6.63 g, 49.8 mmol). The reaction mixture was stirred at 0° C. for 20 min. To this solution at 0° C. was then slowly added zinc chloride in 2-MTHF (1.9 M, 47.7 mL, 90.6 mmol), followed by stirring at room temperature for 16 h. The reaction mixture was quenched with water (300 mL) and extracted with ethyl acetate (3×400 mL). The combined organic layers were dried (Na$_2$SO$_4$) and concentrated under reduced pressure. The resulting crude product was triturated with hexane (2×50 mL) to give benzyl 1-((1R,3r,5S)-8-((((tert-butoxycarbonyl)amino)oxy)(imino)methyl)-8-azabicyclo[3.2.1]octan-3-yl)piperidine-4-carboxylate (Intermediate 10) (22.0 g, 100.0%). The crude product was used without further purification.

LCMS (System 2, Method B): (ESI) m/z 487 [M+H]$^+$ RT 3.10 min, 202 nm.

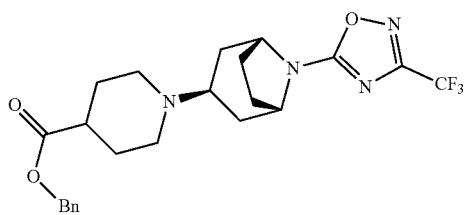 [SMILES: O=C(OCc1ccccc1)C1CCN([C@H]2C[C@H]3CC[C@@H](C2)N3c2nc(C(F)(F)F)no2)CC1]

Step 8: Synthesis of benzyl 1-((1R,3r5S)-8-(3-(trifluoromethyl)-1,2,4-oxadiazol-5-yl)-8-azabicyclo[3.2.1]octan-3-yl)piperidine-4-carboxylate (Intermediate 11)

To a solution of benzyl 1-((1R,3r5S)-8-((((tert-butoxycarbonyl)amino)oxy)(imino)methyl)-8-azabicyclo[3.2.1]octan-3-yl)piperidine-4-carboxylate (Intermediate 10) (22.0 g, 45.3 mmol) in DCM (220 mL) at 0° C. to 5° C. was added dropwise TFA (110 mL, 5 vol). The reaction mixture was stirred at room temperature for 40 min and then cooled to 0° C. to 5° C. To this was then added dropwise TFAA (28.7 mL, 203.7 mmol) and stirred for 30 min before being allowed to warm to room temperature and stirred for 16 h. The reaction mixture was diluted with toluene (220 mL) and concentrated under reduced pressure. Saturated NaHCO$_3$ solution (800 mL) was added and the reaction was extracted with ethyl acetate (3×500 mL). The combined organic layers were dried (Na$_2$SO$_4$) and concentrated under reduced pressure. The resulting residue was purified by column chromatography [Normal-Phase (neutral Al$_2$O$_3$), 0-30% (Ethyl acetate in Hexane)] to give benzyl 1-((1R,3r,5S)-8-(3-(trifluoromethyl)-1,2,4-oxadiazol-5-yl)-8-azabicyclo[3.2.1]octan-3-yl)piperidine-4-carboxylate (Intermediate 11) (12.4 g, 59.0%).

LCMS (System 2, Method B): (ESI) m/z 465 [M+H]$^+$ RT 4.40 min, 240 nm.

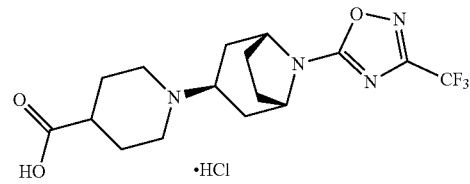 [SMILES: O=C(O)C1CCN([C@H]2C[C@H]3CC[C@@H](C2)N3c2nc(C(F)(F)F)no2)CC1 ; Cl]

Step 9: Synthesis of 1-((1R,3r,5S)-8-(3-(trifluoromethyl)-1,2,4-oxadiazol-5-yl)-8-azabicyclo[3.2.1]octan-3-yl)piperidine-4-carboxylic acid hydrochloride (Intermediate 12)

To a solution of benzyl 1-((1R,3r,5S)-8-(3-(trifluoromethyl)-1,2,4-oxadiazol-5-yl)-8-azabicyclo[3.2.1]octan-3-yl)piperidine-4-carboxylate (Intermediate 11) (12.3 g, 26.5 mmol) in THF (123 mL) and water (24.6 mL) at room temperature was added portion wise lithium hydroxide monohydrate (2.78 g, 66.3 mmol) and was then stirred at room temperature for 16 h. The reaction mixture was diluted with water (100 mL), cooled to 0° C. to 10° C. and pH adjusted to pH=5-6 using 1M HCl solution (approx. 70-80 mL). The reaction mixture was stirred for 1 h and then the aqueous layer was separated and lyophilised to give 1-((1R, 3r, 5S)-8-(3-(trifluoromethyl)-1,2,4-oxadiazol-5-yl)-8-azabicyclo[3.2.1]octan-3-yl)piperidine-4-carboxylic acid hydrochloride (Intermediate 12) (15.1 g, crude). The crude product was used without further purification.

LCMS (System 2, Method B): (ESI) m/z 375 [M+H]$^+$ RT 2.10 min, 236 nm.

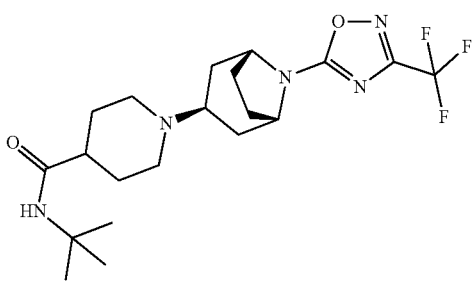 [SMILES: CC(C)(C)NC(=O)C1CCN([C@H]2C[C@H]3CC[C@@H](C2)N3c2nc(C(F)(F)F)no2)CC1]

Step 10: Synthesis of N-(tert-butyl)-1-((1R,3r5S)-8-(3-(trifluoromethyl)-1,2,4-oxadiazol-5-yl)-8-azabicyclo[3.2.1]octan-3-yl)piperidine-4-carboxamide (Intermediate 14)

To a solution of 1-((1R,3r,5S)-8-(3-(trifluoromethyl)-1,2,4-oxadiazol-5-yl)-8-azabicyclo[3.2.1]octan-3-yl)piperidine-4-carboxylic acid hydrochloride (Intermediate 12) (5.8 g, 14.1 mmol) (using 8 g crude isolated from step 9) in DMF (80.0 mL) at 0° C. to 10° C. was added portion wise HATU (12.2 g, 32.0 mmol). The reaction was stirred at 0° C. to 10° C. for 40 min. To this was then added 2-methylpropan-2-amine (CAS: 75-64-9, Intermediate 13) (6.8 mL, 64.2 mmol) and DIPEA (11.4 mL, 64.2 mmol). The resulting reaction mixture was allowed to warm to room temperature and stirred for 16 h. Ice-cold water (500 mL) was added, stirred for 20 min and the precipitate formed was collected by filtration. The filter cake was washed with cold water (500 mL) and then with hexane (500 mL) to give crude product (2.5 g). The aqueous layer was extracted with ethyl acetate (2×200 mL) and the combined organic layers were dried (Na$_2$SO$_4$) and concentrated under reduced pressure to give further crude product (4.5 g). The crude products were combined and purified by column chromatography [Normal-Phase (silica), 0-50% (Ethyl acetate in Hexane)] to give two batches of product with differing purity (2.0 g and 3.8 g). Each batch was then taken separately and purified further by preparative HPLC method A and B respectively. The resulting products were combined and crystallised using IPA (10 vol) and MeOH (1 vol) and the filter cake was washed with cold IPA (2 vol) to give N-(tert-butyl)-1-((1R,3r,5S)-8-(3-(trifluoromethyl)-1,2,4-oxadiazol-5-yl)-8-azabicyclo[3.2.1]octan-3-yl)piperidine-4-carboxamide (Intermediate 14) (1.9 g, 31.4%).

LCMS (System 2, Method B): (ESI) m/z 430 [M+H]$^+$ RT 3.54 min, 240 nm.

$^1$H NMR (400 MHz, DMSO-d6): δ 7.31 (br. s, 1H), 4.39-4.25 (m, 2H), 3.26-3.15 (m, 2H), 2.27-1.80 (m, 10H), 1.71-1.44 (m, 6H), 1.22 (s, 9H).

Step 11: Synthesis of N-(tert-butyl)-1-((1R,3r,5S)-8-(3-(trifluoromethyl)-1,2,4-oxadiazol-5-yl)-8-azabicyclo[3.2.1]octan-3-yl)piperidine-4-carboxamide hydrochloride (Example 1-1)

To a solution of N-(tert-butyl)-1-((1R,3r,5S)-8-(3-(trifluoromethyl)-1,2,4-oxadiazol-5-yl)-8-azabicyclo[3.2.1]octan-3-yl)piperidine-4-carboxamide (Intermediate 14) (1.9 g, 4.4 mmol) in 1,4-dioxane (3.8 mL) at 0° C. was added HCl in 1,4-dioxane (4 M, 19.0 mL, 10 vol). The reaction was stirred at room temperature for 4 h and then concentrated under reduced pressure. The resulting residue was azeotroped with 1,4-dioxane (2×10 mL) and then triturated with 1,4-dioxane (10 mL). The solid was collected by filtration and the filter cake was washed with 1,4-dioxane (2×5 mL), n-pentane (10 mL) and dried under reduced pressure. The solid was crystallised using IPA (10 vol) and MeOH (1 vol) and the filter cake was washed with cold IPA (2 vol) to give N-(tert-butyl)-1-((1R,3r,5S)-8-(3-(trifluoromethyl)-1,2,4-oxadiazol-5-yl)-8-azabicyclo[3.2.1]octan-3-yl)piperidine-4-carboxamide hydrochloride (Example 1-1) (1.8 g, 87.9%).

LCMS (System 2, Method B): (ESI) m/z 430 [M+H]$^+$ RT 3.55 min, 240 nm.

$^1$H NMR (400 MHz, DMSO-d6): δ 10.78-10.24 (m, 1H), 7.58-7.46 (m, 1H), 4.62-4.50 (m, 2H), 3.54-3.43 (m, 2H), 3.32-3.06 (m, 2H), 2.85-2.64 (m, 4H), 2.37-2.20 (m, 1H), 2.13-2.00 (m, 2H), 1.93-1.69 (m, 7H), 1.23 (s, 9H).

Scale up synthesis of N-(tert-butyl)-1-((1R,3r,5S)-8-(3-(trifluoromethyl)-1,2,4-oxadiazol-5-yl)-8-azabicyclo[3.2.1]octan-3-yl)piperidine-4-carboxamide mono hydrochloride mono hydrate (Example 1-2)

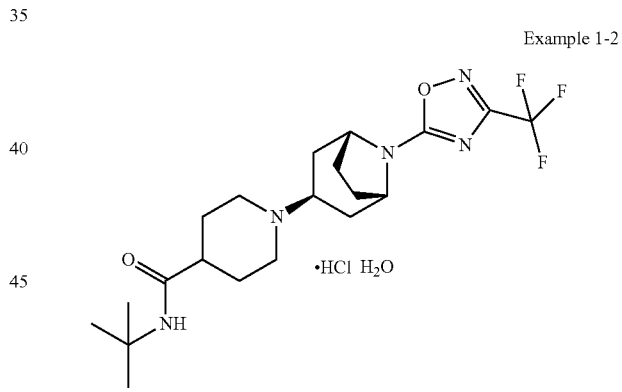

Example 1-2

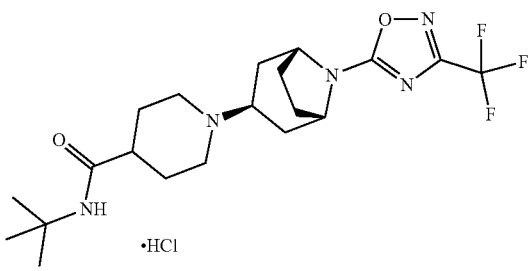 [SMILES: CC(C)(C)NC(=O)C1CCN([C@H]2C[C@H]3CC[C@@H](C2)N3c2nc(C(F)(F)F)no2)CC1 ; Cl]

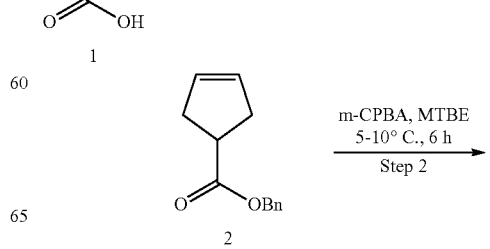

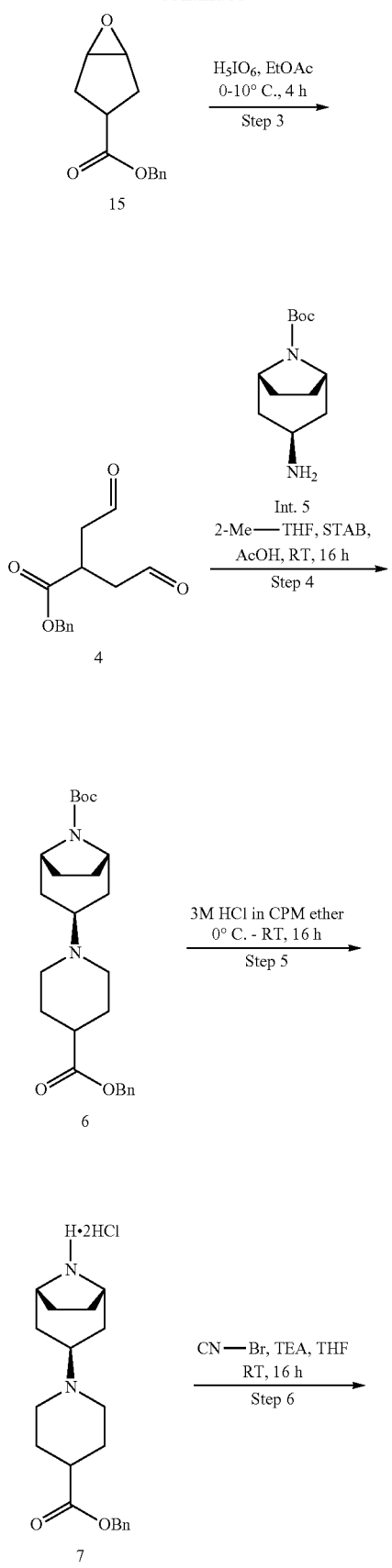
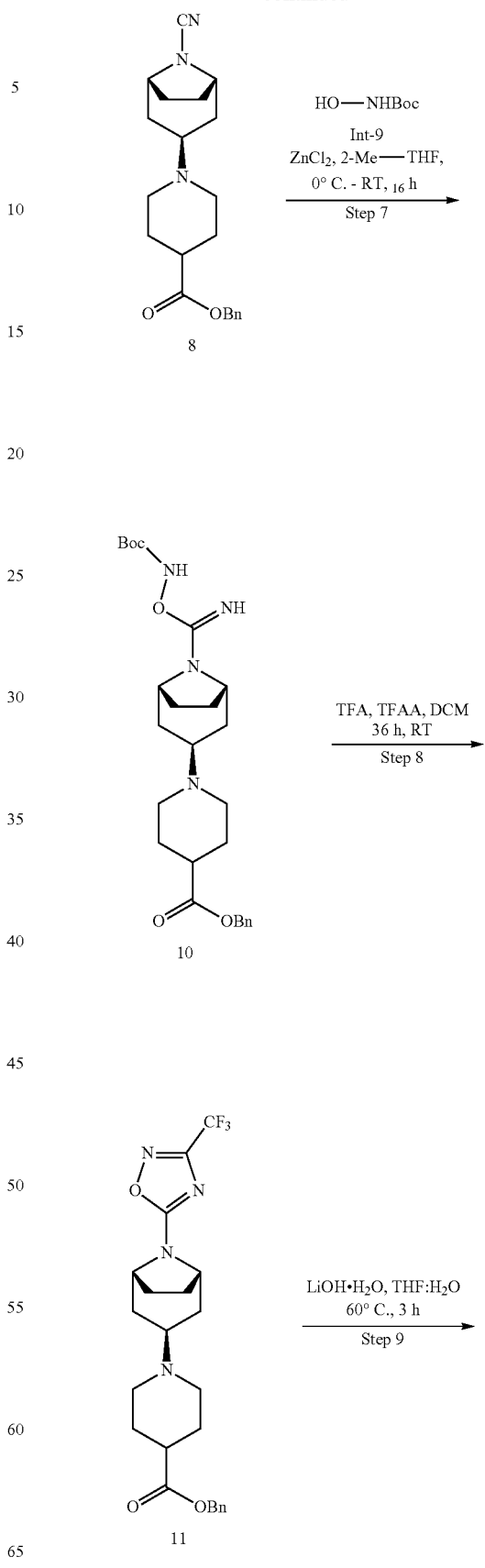

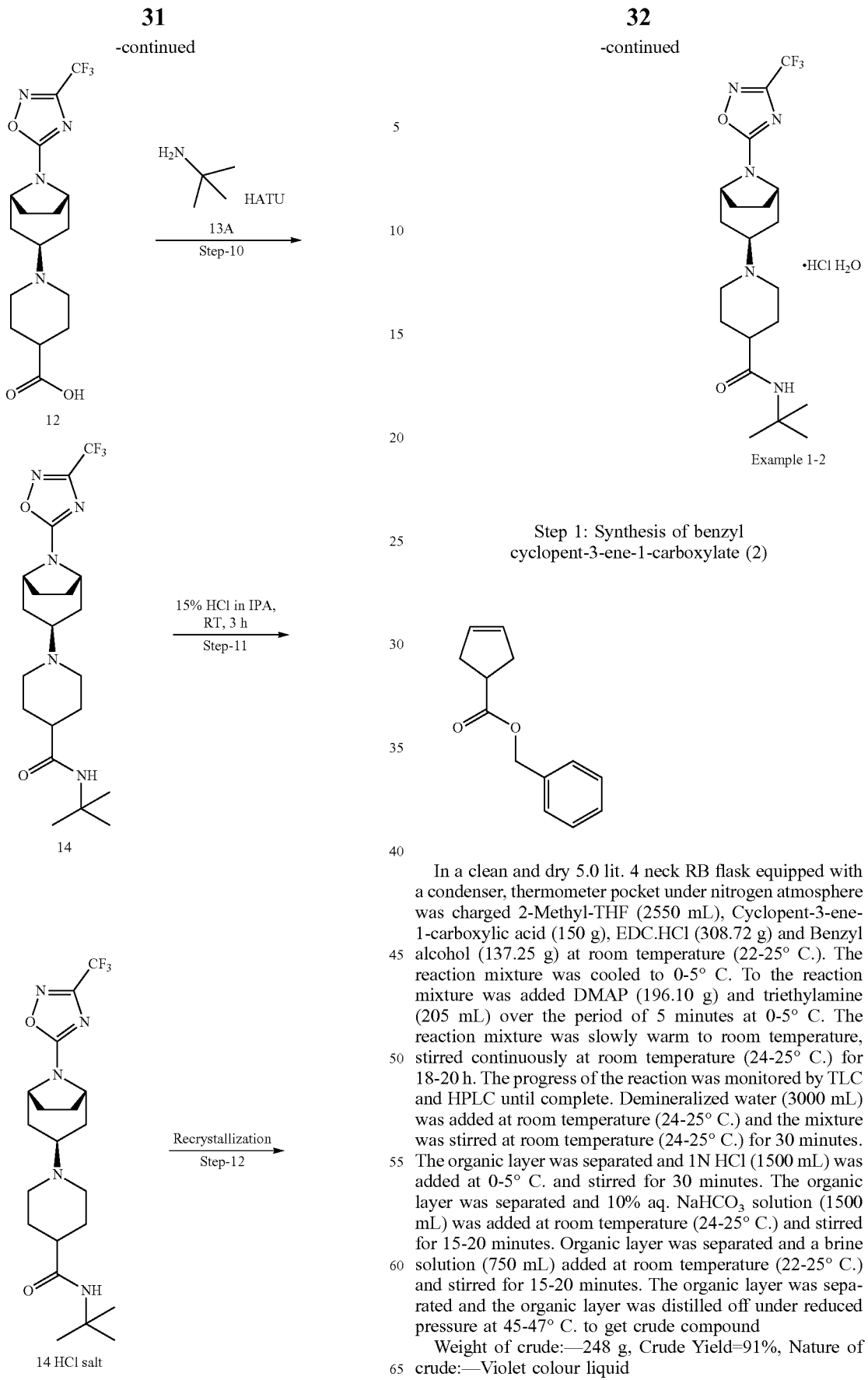

Step 1: Synthesis of benzyl cyclopent-3-ene-1-carboxylate (2)

In a clean and dry 5.0 lit. 4 neck RB flask equipped with a condenser, thermometer pocket under nitrogen atmosphere was charged 2-Methyl-THF (2550 mL), Cyclopent-3-ene-1-carboxylic acid (150 g), EDC.HCl (308.72 g) and Benzyl alcohol (137.25 g) at room temperature (22-25° C.). The reaction mixture was cooled to 0-5° C. To the reaction mixture was added DMAP (196.10 g) and triethylamine (205 mL) over the period of 5 minutes at 0-5° C. The reaction mixture was slowly warm to room temperature, stirred continuously at room temperature (24-25° C.) for 18-20 h. The progress of the reaction was monitored by TLC and HPLC until complete. Demineralized water (3000 mL) was added at room temperature (24-25° C.) and the mixture was stirred at room temperature (24-25° C.) for 30 minutes. The organic layer was separated and 1N HCl (1500 mL) was added at 0-5° C. and stirred for 30 minutes. The organic layer was separated and 10% aq. NaHCO₃ solution (1500 mL) was added at room temperature (24-25° C.) and stirred for 15-20 minutes. Organic layer was separated and a brine solution (750 mL) added at room temperature (22-25° C.) and stirred for 15-20 minutes. The organic layer was separated and the organic layer was distilled off under reduced pressure at 45-47° C. to get crude compound Weight of crude:—248 g, Crude Yield=91%, Nature of crude:—Violet colour liquid This crude was directly used for the next step without further purification.

Step-2: Synthesis of Synthesis of benzyl 6-oxabicyclo 13.1.01 hexane-3-carboxylate (15)

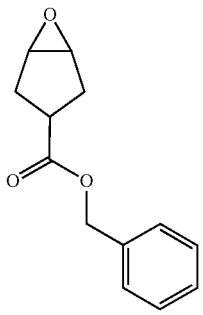 [SMILES: O=C(OCc1ccccc1)C1CC2OC2C1]

In a clean and dry 5.0 lit. 4 neck RB flask with condenser, thermometer pocket under nitrogen atmosphere was charged MTBE (2450 mL) and benzyl cyclopent-3-ene carboxylate (Int-2, 245 g) at room temperature (22-25° C.) and the reaction mixture was cooled to 5-10° C. m-CPBA (362.6 g) was added in 5 separate lots where the colour changes from dark brown to yellow. The reaction mixture slowly warmed to 15-20° C., stirred continuously at 15-20° C. for 16-20 h. The progress of the reaction was monitored by HPLC until completed. A 20% aq. Sodium bisulphite solution (3675 mL, 15 V) was added slowly over the period of 15-20 minutes and stirred at 20-25° C. for 30 minutes. The organic layer was separated and 10% Aq. Na$_2$CO$_3$ solution (2450 mL, 10 V) was added and stirred at 20-25° C. for 15 minutes. The organic layer was separated and 20% aq. Sodium bisulphite solution (2450 mL, 10 V) was added and stirred until peroxide content, <3 mg/lit, peroxide strip. The organic layer was separated and was dried over sodium sulphate, filter, distilled off organic layer under pressure at 37-40° C. to get the benzyl 6-oxabicyclo[3.1.0]hexane-3-carboxylate.

Crude Weight:—234 g, Crude Yield:—88%, Nature of crude:—pale yellow colour liquid This crude was directly used for the next step without further purification.

Step-03: Synthesis of benzyl 4-oxo-2-(2-oxoethyl) butanoate (4)

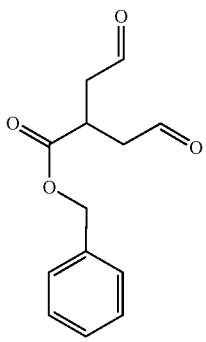 [SMILES: O=CCC(CC=O)C(=O)OCc1ccccc1]

In a clean and dry 2.0 lit. 4 neck RB flask with condenser, Thermometer pocket and under a nitrogen atmosphere was charged Ethyl acetate (380 mL) and periodic acid (87.41 g) at room temperature (22-25° C.) and the white suspension was cooled 0-10° C. Benzyl 6-oxabicyclo[3.1.0] hexane-3-carboxylate (Int-15, 76 g in a 380 mL solution of ethyl acetate) was added and colour changes from dark brown to yellow was observed. The reaction mixture was slowly warmed to 15-20° C. and stirred continuously for 3-4 hrs. The progress of the reaction was monitored by TLC and HPLC until complete. Demineralized water (760 mL, 10 V) was added and stirred at 20-25° C. for 15-20 minutes three separate times. The organic layer was separated and washed with a brine solution (380 mL, 5 V) and stirred at 20-25° C. for 5-10 minutes. The organic layer was separated and dried over sodium sulphate, filtered, distilled off organic layer under pressure at 37-40° C. to get the Benzyl-4-oxo-2-(2-oxoethyl)butanoate.

Crude weight:—82 g, Nature of crude:—pale yellow colour liquid

This crude was directly used for the next step without further purification.

Step-04: Synthesis of tert-butyl (1R,3R,5S)-3-(4-((benzyloxy)carbonyl)piperidin-1-yl) azabicyclo [3.2.1]octane-8-carboxylate (6)

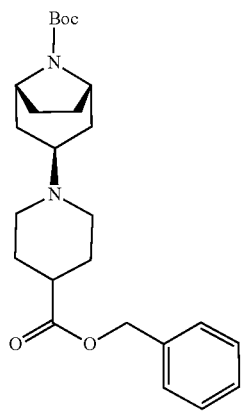 [SMILES: CC(C)(C)OC(=O)N1[C@@H]2CC[C@H]1C[C@@H](N1CCC(C(=O)OCc3ccccc3)CC1)C2]

In a clean and dry 2.0 lit. 4 neck RB flask with condenser and thermometer pocket under a nitrogen atmosphere was charged 2-methyl-THF (570 mL) and benzyl-4-oxo-2-(2-oxoethyl)butanoate (Int-4, 57 g *Actual crude weight was 82 g directly from Step 3) at room temperature (22-23° C.). Int-5 (endo amine) (49.54 g) was added and the reaction was cooled to 5-10° C. and the reaction was stirred for 30 minutes. Sodium triacetoxyborohydride (56.78 g) and glacial acetic acid (5.7 mL) was added and the reaction mixture was warmed to room temperature (22-23° C.) and stirred for 10-12 hrs. The progress of reaction was monitored by TLC and HPLC and upon completion a saturated bicarbonate solution (400 mL, 7 V) was added and stirred at 20-25° C. for 15-20 minutes. The organic layer was separated and was dried over sodium sulphate, filtered, distilled off organic layer under pressure at 37-40° C. to get the tert-butyl (1R,3R,5S)-3-(4-((benzyloxy)carbonyl)piperidin-1-yl)-8-azabicyclo[3.2.1]octane-8-carboxylate.

Weight of crude product:—115 g, Nature of crude:—Thick liquid, Colour:—light maroon Purification using oxalic acid salt formation:

In a clean and dry 500 mL, 4 neck RB flask with Thermometer and condenser charge crude (25 g) and Acetone (150 mL, 6V) and cool to 5-10° C. Charge oxalic acid (10 g, 2.0 eq.) and warm the reaction mass warm to rt with stirred for 2 h. Distilled out reaction mass at 40° C. to afford a crude weight:—35 g then charge 10 Vol MTBE at 25-30° C. and stirred for 30 minutes. Filter the reaction mass, bed wash with MTBE (1.0 vol) to afford wet solid (Oxalate salt):—26 g. The solid was suspended into Saturated bicarbonate solution (30 vol, 780 mL) and Ethyl acetate (25 Vol, 650 mL) and Stirred for 15 minutes. The organic layer was separated, dried over Na$_2$SO$_4$, distilled out under vacuum at 37-40° C. to get the product.

Weight of product:—8.0 g

Optionally this material can be additionally purified column chromatography using hexane: ethyl acetate, adsorption on neutral alumina (Source-SDFCL). Column gradient: 5→10→12% Ethyl acetate: Hexane.

Step-05: Synthesis of benzyl 1-((1R,3R,5S)-8-azabicyclo[3.2.1]octan-3-yl)piperidine carboxylate hydrochloride (7)

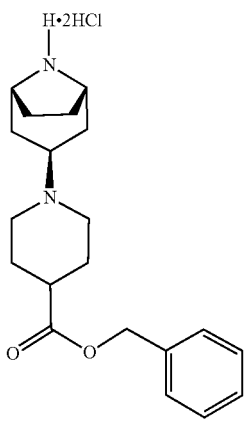

In a clean and dry 5.0 lit. 4 neck RB flask with condenser and thermometer pocket under nitrogen atmosphere was charged, cyclopentyl methyl ether (452 mL, 4.0 V) and Int-6 (113 g, 1.0 eq.) and the reaction mixture was cooled to 0-5° C. 3M HCl in cyclopentyl methyl ether (904 mL, 8.0 V) very slowly at 0-5° C. and the reaction mixture was slowly warm to 22-25° C. and stirred for 16 h. Reaction was monitored by HPLC until completed. The reaction mixture was filtered under a N$_2$ atmosphere, bed wash with MTBE (2.0 vol.), unloaded the wet cake of product under N$_2$, and dried under reduced pressure at 45-47° C. to get crude that was directly used in the next step without any further purification.

Step-06: Synthesis of benzyl 1-((1R,3R,5S)-8-cyano-8-azabicyclo[3.2.1]octan-3-yl)piperidine-4-carboxylate (8)

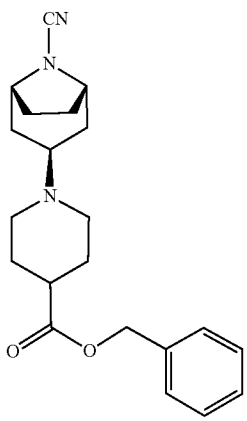 [SMILES: N#CN1[C@@H]2CC[C@H]1C[C@@H](N1CCC(C(=O)OCc3ccccc3)CC1)C2]

In a clean and dry 5.0 lit. 4 neck RB flask with condenser and Thermometer pocket under nitrogen atmosphere was charged dichloromethane (1860 mL, 10 vol.), Int-7 (186.0 g, 1.0 eq.) and triethylamine (355 mL, 5.0 eq.) at 22-25° C. over the period of 10-15 minutes and further stirred the reaction mixture for 30-45 minutes. The reaction mixture was cooled to 0-5° C. and cyanogen bromide (92 g, 1.7 eq.) in DCM (372 mL, 2.0 V) at 0 −5° C. was added and the reaction mixture was slowly warm to 22-25° C. and stirred at 22-25° C. for 3-4 h. The progress of the reaction was monitored by HPLC until complete. The reaction mixture was diluted with DCM (1860 mL, 10 vol.), basified using sat. NaHCO$_3$ solution (930 mL, 5V). The organic layer was separated and the aq. Layer was extracted with DCM (1860 mL, 10 vol). The combined organic layer was dried over Na$_2$SO$_4$ and evaporated under reduced pressure to give 190 g of crude compound. The crude compound was purified by neutral alumina column chromatography by using 15% ethyl acetate in hexane. Pure fractions were collected and concentrated under reduced pressure to give 75 g of pure compound. (Yield: 46%).

Step-07: Synthesis benzyl 1-((1R,3R,5S)-8-((((tert-butoxycarbonyl)amino)oxy)(imino)methyl)-8-azabicyclo[3.2.1]octan-3-yl)piperidine-4-carboxylate (10)

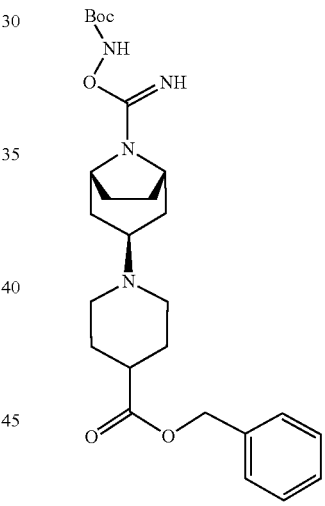

In a clean and dry 3.0 lit. 4 neck RB flask with condenser and thermometer pocket under nitrogen atmosphere was charged 2-Methyl THF (800 mL, 10 vol.) and Int. 8 (80 g, 1.0 eq.) and the reaction mixture was cooled to 0-5° C. A solution of ZnCl$_2$ (2.2 eq., 1.9 M solution in 2-Methyl-THF) was added and the reaction mixture was stirred at 0° C. for 30 minutes, then N-Boc-hydroxyl amine (Int-9) (1.2 eq.) was added and the reaction mixture slowly warm to 23-25° C. and stirring was continued for 16 h. The progress of the reaction was monitored by TLC and HPLC until complete. The reaction mixture was quenched with water (800 mL, 10.0 V) and then product was extracted with ethyl acetate (2×800 mL). The combined organic layer was dried over Na$_2$SO$_4$ and evaporated under reduced pressure to give 110 g (quantitative yield) of crude compound. This product was directly used in the next step without any further purification.

Step-08: Synthesis of benzyl 1-((1R,3R,5S)-8-(3-(trifluoromethyl)-1,2,4-oxadiazol-5-yl) azabicyclo[3.2.1]octan-3-yl)piperidine-4-carboxylate (11)

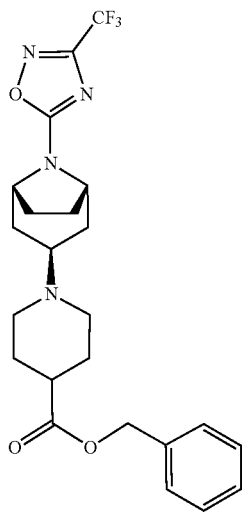 [SMILES: O=C(OCc1ccccc1)C1CCN([C@H]2C[C@H]3CC[C@@H](C2)N3c2nc(C(F)(F)F)no2)CC1]

In a clean and dry 3.0 lit. 4 neck RB flask with condenser and thermometer pocket under nitrogen atmosphere was charged DCM (1150 mL, 10.0 vol.) and Int-10 (115.0 g, 1.0 eq.) and the reaction mixture was cooled to 0-5° C. A mixture of trifluoroacetic acid (271 mL, 15.0 eq.) and TFAA (164 mL, 5.0 eq.) was added by drop-wise addition in 3 separate lots at 0-5° C. with an interval of 3-4 h under nitrogen atmosphere. The reaction mixture was stirred at RT for 12 h then a further 16 h until the progress of the reaction was completed (monitored by TLC and HPLC). After completion of the reaction, the reaction mixture was cooled to 0° C. and the pH (7-8) was adjusted using saturated aq. NaHCO$_3$ solution and stirred the reaction mixture for 15 min. The layers were separated and the aqueous layer was extracted with DCM (2×100 mL). The combined organic layer was dried over Na$_2$SO$_4$ and evaporated under reduced pressure to give 145 g of crude compound, which was purified by column chromatography using neutral alumina using hexane and ethyl acetate as an eluent to get the pure 49 g product.

Step-09: Synthesis of 1-((1R,3R,5S)-8-(3-(trifluoromethyl)-1,14-oxadiazol-5-yl)-8-azabicyclo[3.2.1]octan-3-yl)piperidine-4-carboxylic acid (12)

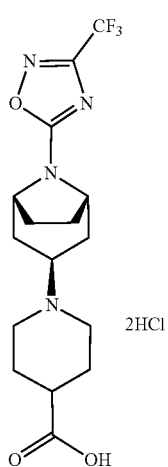 [SMILES: O=C(O)C1CCN([C@H]2C[C@H]3CC[C@@H](C2)N3c2nc(C(F)(F)F)no2)CC1]

In a clean and dry 5.0 lit. 4 neck RB flask equipped with a condenser and thermometer pocket under nitrogen atmosphere was charged THF (2250 mL) demineralized water (450 mL) and Int. 11 (225 g) at room temperature (22-25° C.). Lithium hydroxide monohydrate (30.5 g, 2.0 eq.) was added at room temperature (22-25° C.) and the reaction mixture was stirred at 60° C. for 4 h. The progress of the reaction was monitored TLC and HPLC and after completion of the reaction, the reaction mixture was cooled to 0-5° C. The pH was adjusted to 4-5 by using 1N HCl solution and the mixture was stirred it for 15 min. The solvent was evaporated and the crude product was purified once MTBE (10.0 V) was added to the crude solid compound at RT, and stirred for 2 h at RT. The solid was filtered, washed with MTBE (1.0 V). The solid compound was dried under vacuum to afford 245 g (*Actual compound is 216 g of Int-12 and remaining approx. 29.0 g is lithium chloride salt) of the product as off white solid.

Step-10: Synthesis of N-(tert-butyl)-1-((1R,3r,5S)-8-(3-(trifluoromethyl)-1,2,4-oxadiazol-5-yl)-8-azabicyclo[3.2.1]octan-3-yl)biperidine-4-carboxamide

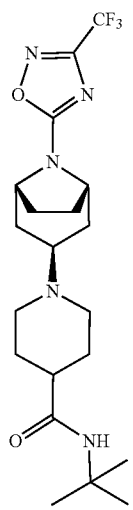 [SMILES: CC(C)(C)NC(=O)C1CCN([C@H]2C[C@H]3CC[C@@H](C2)N3c2nc(C(F)(F)F)no2)CC1]

Procedure:

In a clean and dried 3 neck 1 L round bottom flask equipped with a mechanical stirrer and Nitrogen inlet was charged with acetonitrile (20.0 V) and Int-12 (1.0 eq) in a single lot and stirred the reaction mass for 10 min. The reaction mixture was cooled to 0° C. and then HATU was added followed by tert-butylamine (1.5 eq), DIPEA (4.0 V) slowly up to 15 min. After complete addition the reaction mixture was stirred at room temperature for 16 h. The progress of the reaction was monitored TLC and once completed the excess acetonitrile was distilled out under reduced pressure. The reaction was quenched with demineralized water (40.0 V) and solid material precipitates out and stirred for 60 min. The solid was washed with demineralized water (5.0 V) and dried by suction. The solid compound was dried under vacuum to afford 56.0 g of the product as off white solid.

Step-11: Synthesis of N-(tert-butyl)-1-((1R,3r,5S)-8-(3-(trifluoromethyl)-1,2,4-oxadiazol-5-yl)-8-azabicyclo[3.2.1]octan-3-yl)piperidine-4-carboxamide hydrochloride salt

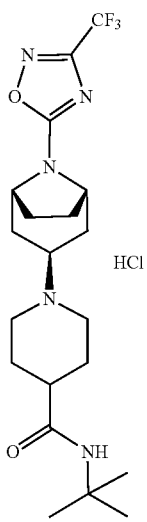 [SMILES: CC(C)(C)NC(=O)C1CCN([C@H]2C[C@H]3CC[C@@H](C2)N3c2nc(C(F)(F)F)no2)CC1 ; Cl]

In a flask was taken Int-14 free base (56.0 g, 1.0 eq.) in Acetone (10.0 V) and stirred the reaction mixture for 10 min. Then reaction mixture was then allowed to cool to 0° C. and a solution of 15% HCl in IPA at 0° C. was added dropwise. Then reaction mixture was allowed to come warm to 25-30° C. and stirred for 2 h at 25-30° C. Solvent was evaporated completely under reduced pressure and co-distilled 2 times with 10.0V n-heptane. The solid compound was dried under vacuum to afford 59.0 g of the product as off white solid.

Step-12: Recrystallization: Synthesis of N-(tert-butyl)-1-((1R,3r,5S)-8-(3-(trifluoromethyl)-1,2,4-oxadiazol-5-yl)-8-azabicyclo[3.2.1]octan-3-yl)piperidine-4-carboxamide monohydrochloride monohydrate (Example 1-2)

A flask was charged with Int-14 HCl salt (108.0 g) in IPA (10.0 V) and the reaction mixture was heated to reflux for 1 h, however, the solid not completely soluble at reflux temperature. MeOH (1.0 V) was added with continue heating for 1 h and a solution was obtained. The hot solution was passed through filter paper to remove insoluble particles. The solvent (approx. 8 volumes out of 11 volumes of solvent) was removed under reduced pressure. Then approx. 3 volumes solvent remained and allowed to cool to 0° C. and stirred for 1 h at the same temperature. Then solid was filtered and wash with a minimum amount of chilled IPA and dried via suction. The solid compound was dried under vacuum to afford 93.5 g of the product as off white solid.

An analysis was performed to determine the composition of the batch. The conclusion is that this batch is a monohydrochloride mono-hydrate.

Formula of mono-hydrochloride mono-hydrate: $C_{20}H_{33}N_5O_3ClF_3$ Molecular weight: 483.96

N-(tert-butyl)-1-((1R,3r,5S)-8-(3-(trifluoromethyl)-1,2,4-oxadiazol-5-yl)-8-azabicyclo[3.2.1]octan-3-yl)piperidine-4-carboxamide monohydrochloride monohydrate

| | % theory | % measured | measured vs theory |
|---|---|---|---|
| Carbon | 49.64% | 49.56% | 99.85% |
| Hydrogen | 6.87% | 6.89% | 100.25% |
| Nitrogen | 14.47% | 14.45% | 99.86% |
| Chlorine | 7.33% | 7.28% | 99.38% |
| Water | 3.72% | 4.33% | 116.40% |

Biological Activity

Example A: Phospho-ERK1/2 Assays

Functional assays were performed using the Alphascreen Surefire phospho-ERK1/2 assay (Crouch & Osmond, Comb. Chem. High Throughput Screen, 2008). ERK1/2 phosphorylation is a downstream consequence of both Gq/11 and Gi/o protein coupled receptor activation, making it highly suitable for the assessment of $M_1$, $M_3$ (Gq/11 coupled) and $M_2$, $M_4$ receptors (Gi/o coupled), rather than using different assay formats for different receptor subtypes. CHO cells stably expressing the human muscarinic $M_1$, $M_2$, $M_3$ or $M_4$ receptor were plated (25K/well) onto 96-well tissue culture plates in MEM-alpha+10% dialysed FBS. Once adhered, cells were serum-starved overnight. Agonist stimulation was performed by the addition of 5 μL agonist to the cells for 5 min (37° C.). Media was removed and 50 μL of lysis buffer added. After 15 min, a 4 μL sample was transferred to 384-well plate and 7 μL of detection mixture added. Plates were incubated for 2 h with gentle agitation in the dark and then read on a PHERAstar plate reader. $pEC_{50}$ and $E_{max}$ figures were calculated from the resulting data for each receptor subtype and the results are set out in Table 1 below.

TABLE 1

| | Muscarinic Activity | | | |
|---|---|---|---|---|
| Example No. | $pEC_{50}$ M1 (% Emax cf. ACh) | $pEC_{50}$ M2 (% Emax cf. ACh) | $pEC_{50}$ M3 (% Emax cf. ACh) | $pEC_{50}$ M4 (% Emax cf. ACh) |
| Acetylcholine (ACh) | 8.05 (96) | 7.73 (106) | 8.27 (102) | 8.00 (108) |
| 1-1 | 7.17 (92) | <4.70 (7) | <4.70 (3) | 6.92 (32) |

Example B: CLint (in vitro hepatocytes) (Example 1)

Hepatocyte stability assays were performed using pooled cryopreserved hepatocytes (Bioreclamation). Test compounds prepared in DMSO, were incubated at an initial concentration of 1 μM (0.25% DMSO final, n=2) with hepatocytes at cell densities of 1.0 million cells/mL at 37° C. Aliquots were removed at 0.5, 5, 10, 15, 30, 60 and 120 minutes for termination of reactions and compound extraction with acetonitrile containing an analytical internal standard (0.5 μM carbamazepine). Samples were centrifuged and the supernatant fractions analysed for parent compound by mass spectrometry (LC-MS/MS). The amount of compound remaining (expressed as %) was determined from the MS response in each sample relative to that in the T=0 samples (normalised for internal standard). Ln plots of the % remaining were used to determine the half-life for compound disappearance using the relationship:

Half-Life(min)=−0.693/λ (where λ is the slope of the Ln % remaining vs time curve).

The in vitro intrinsic clearance (CLint) as pUmin/million cells was calculated using the formula:

Clint(µL/min/million cells)=(0.693/Half-Life(min))× (1000/million cells per mL incubation)

Mouse=7 uL/min/million
Rat 8 uL/min/million
Dog 8 uL/min/million
Monkey <5 uL/min/million
Human <5 uL/min/million Example C: MDCK Permeability/Efflux (Example 1)

MDR1-MDCK cells (Solvo Biotechnology) were seeded onto 24-well Transwell plates at $2.35 \times 10^5$ cells per well and used in confluent monolayers after a 3 day culture at 37° C. under 5% CO2. For cell types, test and control compounds (propranolol, vinblastine) were added (1 µM, 0.1% DMSO final, n=2) to donor compartments of the Transwell plate assembly in assay buffer (Hanks balanced salt solution supplemented with 25 mM HEPES, adjusted to pH 7.4) for both apical to basolateral (A>B) and basolateral to apical (B>A) measurements. Incubations were performed at 37° C., with samples removed from both donor and acceptor chambers at T=0 and 1 hour and compound analysed by mass spectrometry (LC-MS/MS) including an analytical internal standard.

Apparent permeability (Papp) values were determined from the relationship:

Papp=(CompoundAcceptor T=end/(CompoundDonor×VDonor)Incubation Time)×VDonor Area× $60 \times 10^{-6}$ cm/s Where V is the volume of each Transwell compartment (apical 125 µL, basolateral 600 µL), and concentrations are the relative MS responses for compound (normalized to internal standard) in the donor chamber before incubation and acceptor chamber at the end of the incubation. Area=area of cells exposed for drug transfer (0.33 cm$^2$). Efflux ratio (Papp B>A /Papp A>B) was calculated from the mean Papp values in each direction. The MDR1-MDCK cell line has been engineered to over-express the efflux transporter, MDR1 (P-glycoprotein), and a finding of good permeability B>A, but poor permeability A>B, suggests that a compound is a substrate for this transporter. Lucifer Yellow (LY) was added to the apical buffer in all wells to assess viability of the cell layer. As LY cannot freely permeate lipophilic barriers, a high degree of LY transport indicates poor integrity of the cell layer and wells with a LY Papp >$10 \times 10^{-6}$ cm/s were rejected. Note that an integrity failure in one well does not affect the validity of other wells on the plate. Compound recovery from the wells was determined from MS responses (normalized to internal standard) in donor and acceptor chambers at the end of incubation compared to response in the donor chamber pre-incubation. Recoveries <50% suggest compound solubility, stability or binding issues in the assay which may reduce the reliability of a result.

A−B=$66 \times 10^{-6}$ cm/sec
B−A=$77 \times 10^{-6}$ cm/sec
B−A/A−B efflux ratio=1.2

Example D: Solubility Data (Example 1)

Aqueous Solubility (Thermodynamic)—LCMS/MS Method

A 10 mM stock solution (in DMSO) was prepared for the test sample. From the 10 mM stock solution, a working solution of 1 µM was prepared by diluting the test sample in mobile phase solution (typically, methanol: 2 mM ammonium acetate containing suitable internal standard (IS)—carbamazepine/any other suitable IS). Further, the working solution was serially diluted in mobile phase solution up to 5 to 6 linearity point to prepare standard solution for plotting calibration curve. The area for each standard sample is analyzed in singlet using LCMS/MS. The normalized area values are plotted vs. concentration to achieve calibration equation to determine the unknown sample. For ascertaining the aqueous thermodynamic (TD) solubility of test compound, 1 mg (powder form of the) compound is added to 1 mL of each buffer and bio relevant media mentioned in table below to achieve a theoretical concentration equivalent to 1 mg/mL. Test compound was dispersed in buffer solution using a vortex mixer.

| Sr No. | Name of the Reagent |
|---|---|
| 1 | SGF pH-1.2 |
| 2 | Blank FaSSIF (Aq. Buffer) pH-6.5 |
| 3 | FaSSIF pH-6.5 |

The resulting solution are then kept on RotoSpin (shaker) at 50 rpm for 4 hours for TD solubility at room temperature (25° C.). After the incubation period, the solution is filtered using 0.45 micron PVDF injector filters in order to remove the insoluble fraction of the compound. Filtrate is diluted in mobile phase and subsequently the AUC is ascertained for diluted samples using LCMS/MS. From the AUC of test sample the corresponding concentration is calculated using 5 to 6 point linearity/calibration curve.

All numbers reported as uM.

| Blank FaSSIF pH 6.5 (n = 4) | FaSSIF pH 6.5 (n = 4) | SGF pH 1.2 (n = 4) |
|---|---|---|
| 1743 | 2008 | 2079 |
| 1941 | 2448 | 1988 |
| 1937 | 1713 | 1702 |
| 2022 | 2104 | 2039 |

Example E: HµREL (Example 1)

Upon arrival of HµREL human Pool™ 96-well hepatic co-culture plates, media was replaced and cells allowed to acclimatise at 37° C. for ~20 hr. HµREL® incubation media (serum free) and test compound (final substrate concentration 1 µM; final DMSO concentration 0.1%) were added to the HµREL® 96-well co-culture system (final cell number of 30,000 cells per well) to initiate the reaction. The final incubation volume was 80 µL per time point. Two control compounds were included per assay. All incubations were performed singularly for each test compound.

Each compound was incubated for 0, 2, 6, 24, 48 and 72 hr (0, 120, 360, 1440, 2880 and 4320 min). The reactions were stopped by transferring 60 µL of incubate to 180 µL acetonitrile containing internal standard at the appropriate time points. The termination plates were centrifuged at 3000 rpm at 4° C. for 20 min to precipitate any residual protein.

Quantitative Analysis

Following protein precipitation, the sample supernatants were combined in cassettes of up to 4 compounds and analysed using Cyprotex generic LC-MS/MS conditions.

Data Analysis

From a plot of ln peak area ratio (compound peak area/internal standard peak area) against time, the gradient of the line was determined. Subsequently, half-life ($t_{1/2}$) and intrinsic clearance ($CL_{int}$) were calculated using the equations below:

Elimination rate constant $(k) = (-\text{gradient})$ $$\text{Half-life}(t_{1/2})(\text{min}) = \frac{0.693}{k}$$

$$\text{Intrinsic clearance } (CL_{int})(\mu L/\text{min}/\text{million cells}) = \frac{V \times 0.693}{t_{1/2}}$$

(where $V$ = Incubation volume ($\mu$L)/Number of cells)

$CLint < 0.143\ uL/\text{min}/\text{million}$

Example F: Predicted Target Engagement for Human Efficacious Dose (Example 1)

The expected requirement for observing $M_1$ agonist efficacy in humans is 6 hours unbound brain exposure over the recombinant $M_1$ $EC_{50}$. Example 1 is predicted to reach the unbound brain exposure required for $M_1$ agonist efficacy at a dose of approx. 22 mg and has a predicted human half-life of 15 h (FIG. 1).

Parameters used in Receptor occupancy prediction (Target Engagement).

MW=429.48
$M_1$ $pEC_{50}$=7.17
Fu=0.682
Kpuu=1
Half-life (predicted)=15 h
F=0.61
Cl=4.4 ml/min/kg
V=5.9 ml/min/kg
Ka=1

Definitions:

fu—fraction of compound unbound in plasma or brain tissue homogenate

F—bioavailability; the percentage of an administered dose that reaches the systemic circulation (plasma)

Kp,uu—ratio of unbound brain concentration/unbound plasma concentration. Quantifies the net flux of drug across the blood brain barrier, including the quantitative role of transporters, without being confounded by nonspecific binding in plasma and brain tissues. Gupta et al, DMD, 2006; Hammarlund-Udenaes et al, PharmRes, 2008

Example G: Attenuation of Sub-Chronic PCP-Induced Deficit in the Operant Reversal Learning Task in Female Lister Hooded Rats (Example 1)

Aim and Outcomes

Investigate the ability of Example 1 (1, 3, 10 and 30 mg/kg, p.o., 1 hour pre-treatment time ptt) to attenuate the disruption of a cognitive task induced by sub-chronic treatment with phencyclidine (scPCP) in female Lister Hooded rats.

There was a significant ($P<0.01$) reduction in percent correct responding in the reversal phase of the task in the scPCP group compared to vehicle (FIG. 2). Treatment with Example 1 at the lowest and two middle doses (1, 3 and 10 mg/kg) significantly ($P<0.05$, $P<0.05$ and $P<0.01$ respectively) increased percent correct responding compared to the scPCP group in the reversal phase (FIG. 2).

Materials and Methods

Female Lister Hooded rats were used for this experiment. The average weight of rats at the time of testing was 294 g±29 g. Rats were housed in groups of 3-5 under standard laboratory conditions under a 12 hr light: dark cycle (lights on at 0700 hr), and food restricted to 90% of free-feeding bodyweight (12 g of food per rat per day). Testing was carried out in the light phase. Rats were randomly assigned to two treatment groups and received vehicle, n=8 (0.9% saline solution, i.p.) or PCP, n=48 (2 mg/kg, i.p. twice daily for 7-days). On the day of testing, rats were randomly assigned to seven treatment groups (n=6-8 per group) to receive an acute treatment with Example 1 (1, 3, 10 and 30 mg/kg, p.o., 1 hour ptt) or vehicle. Example 1 was dissolved in 1% methylcellulose and administered orally (p.o.) in a volume of 5 ml/kg, 1 hour prior to testing. The study was carried out in accordance with the Animals Scientific Procedures Act (UK, 1986) and was approved by the University of Manchester AWERB (Animal Welfare and Ethical Review Body).

Experimental Procedure

Following habituation to the operant chambers, rats were trained to respond for food on an FR1 (Fixed Ratio 1) schedule of reinforcement with both levers active. When responding was stabilised, rats were trained to press either the left or right lever for food delivery and the active lever was varied from day to day. Each session lasted 20 minutes and counts were recorded on each lever. Subsequently the rats were then trained to respond for food according to the position of a visual cue (a lit LED). Half were trained to press the lever under the lit LED in order to receive a food reward, the other half were trained on the opposite contingency (to press the lever under the non-lit LED). The experimental session was terminated following a total of 128 lever presses, which took approximately 30 minutes. Subsequently, rats were trained until they again reached criterion on the opposite contingency.

The day before each reversal learning task session, a full 30-minute operant training session (as described above) was conducted to ensure stable responding. For the reversal learning task animals were first exposed to a 5-minute period during which the contingency (cue position relative to active lever) was the same as for the operant training session. During this period, responses on both correct and incorrect levers were recorded. This part of the session is termed the initial phase. In the subsequent 5-minute period, the contingency was reversed. Responses made on the correct and incorrect levers were again recorded. This second period is termed the reversal phase. At this stage, training ceased and rats were treated with PCP (2 mg/kg, i.p. or vehicle 0.9% saline, i.p.) for 7 days followed by at least a 7-day washout period. Rats were randomized such that all rats within a cage received a different drug treatment.

Data are presented as percent correct response (±S.E.M) with values for the initial and reversal phases are presented for the different drug treatment groups (FIG. 2). The percentage correct response data were used to determine whether there was a significant effect of drug on response accuracy (e.g. that might reflect cognitive dysfunction); Statistical significance was assumed when $P<0.05$ and was determined using one-way ANOVA in order to detect main effect of drug treatment in the initial and reversal phases. The total number of lever presses recorded during both the initial and reversal phases were not significantly different following treatment with either vehicle or Example 1 (Table 2) confirming an absence of non-specific effects on general response in this study.

TABLE 2

The effect of acute treatment with Example 1 (1.0, 3.0, 10.0 & 30.0 mg/kg, p.o.) in scPCP treated rats (2 mg/kg, i.p. twice daily for seven days, followed by at least a 7-day washout period) on general performance in the reversal learning task. Data are shown as the mean total number of lever presses in the initial and retention phases of a reversal learning task ± S.E.M (n = 6-9).

| Drug treatment | Initial phase | Reversal phase |
| --- | --- | --- |
| scSaline + Vehicle | 27.0 ± 0.2 | 27.3 ± 0.2 |
| scPCP + Vehicle | 26.5 ± 0.2 | 26.0 ± 0.5 |
| scPCP + Example 1 1.0 mg/kg | 27.4 ± 0.2 | 27.5 ± 0.3 |
| scPCP + Example 1 3.0 mg/kg | 27.5 ± 0.2 | 26.8 ± 0.2 |
| scPCP + Example 1 10.0 mg/kg | 27.0 ± 0.3 | 26.6 ± 0.5 |
| scPCP + Example 1 30.0 mg/kg | 26.4 ± 0.6 | 26.6 ± 0.3 |

BRIEF DESCRIPTION OF THE FIGURES

FIG. 1 shows the predicted target engagement for efficacious dose of Example 1 from allometric scaling across mouse, rat, dog and monkey species following oral administration. Data are shown as a function of the calculated % $M_1$ receptor target engagement where 50% is equivalent to an unbound exposure equal to the recombinant human EC50 (86 nM or 28 ng/ml). Based on a measured equivalent unbound plasma:brain distribution profile (Kpuu=1) the exposures shown represent those in either the plasma or brain compartment.

FIG. 2 shows the effect of acute treatment with Example 1 (1.0, 3.0, 10.0 & 30.0 mg/kg, p.o.) in scPCP treated rats (2 mg/kg, i.p. twice daily for seven days, followed by at least a 7-day washout period) on performance in the reversal learning task. Data are shown as mean correct responding %±S.E.M. (n=6-9). The dashed line separates the initial phase (left) from the reversal phase of the task (right). Data were analysed by one-way ANOVA followed by LSD test. ***P<0.001; significant reduction in correct responding % in reversal phase of the task compared to the scSaline+Vehicle group. #P<0.05; ##P=0.01; ###P<0.001; significant increase in correct responding % in reversal phase of the task compared to the scPCP+Vehicle group.

EQUIVALENTS

Figure 1:
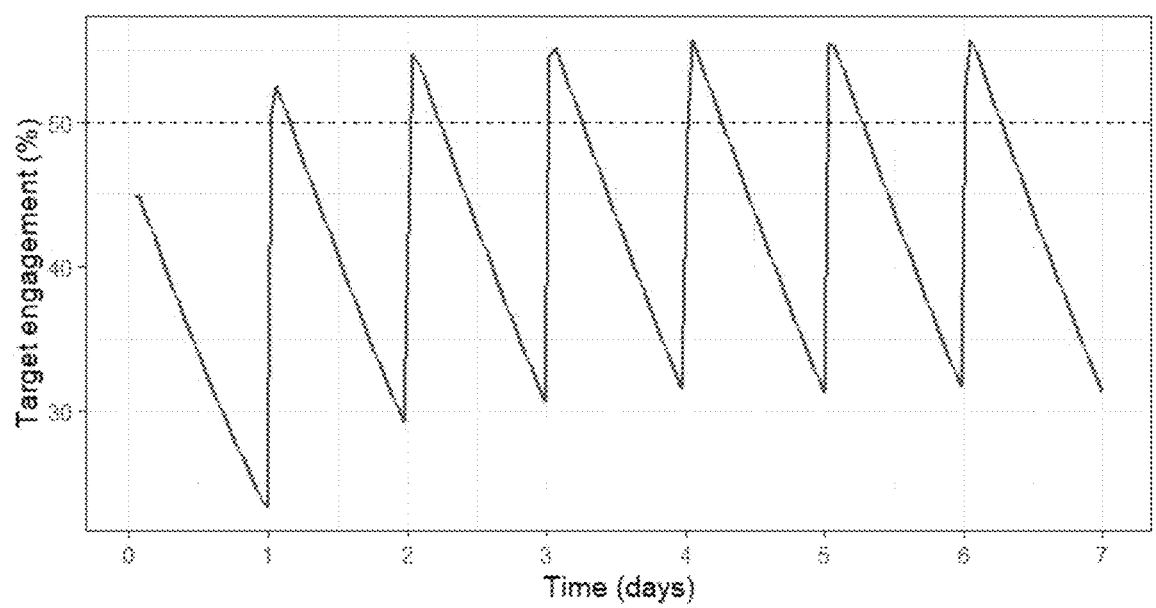
FIG. 1.
Figure 2:
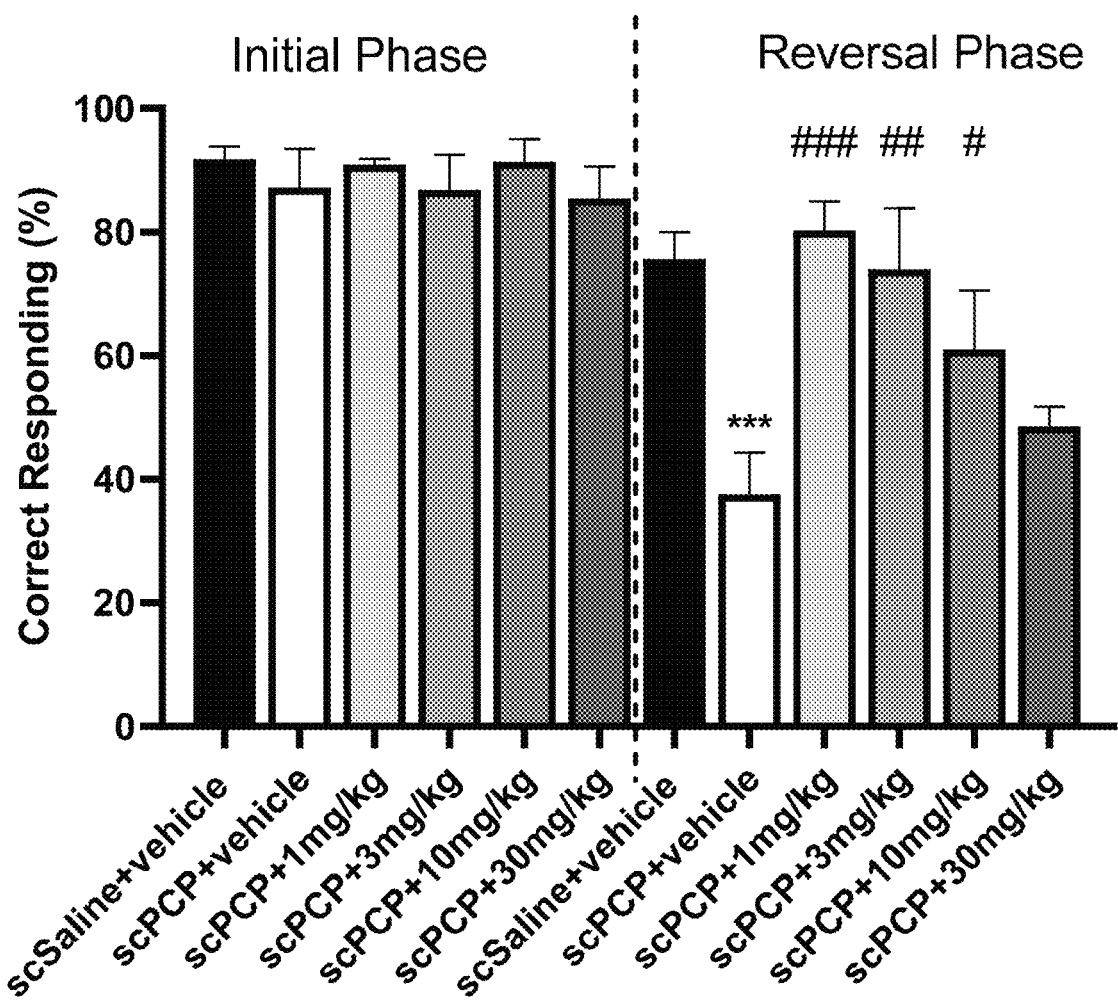
FIG. 2.

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of formula (1):

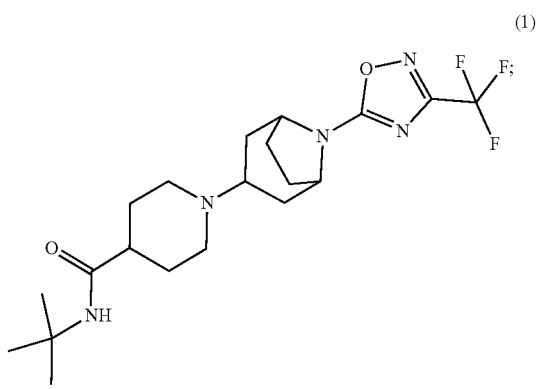 [SMILES: CC(C)(C)NC(=O)C1CCN(C2CC3CCC(C2)N3c2nc(C(F)(F)F)no2)CC1]

or a salt thereof.

2. The compound according to claim 1, which is a compound of formula (2):

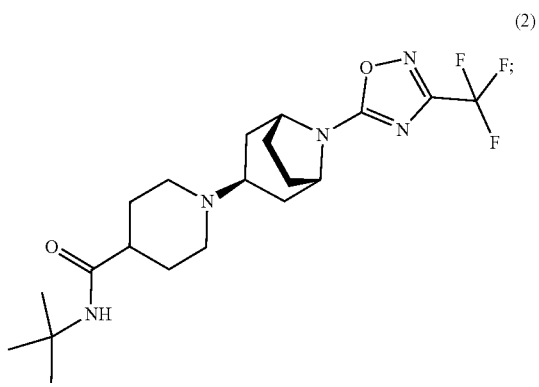

or a salt thereof.

3. A salt of the compound according to claim 1.
4. A pharmaceutically acceptable salt of the compound according to claim 1.
5. An acid addition salt of the compound according to claim 1.
6. A hydrochloride salt of the compound according to claim 1.
7. A monohydrochloride salt of the compound according to claim 1.
8. The compound according to claim 1, which is a compound of formula (2b):

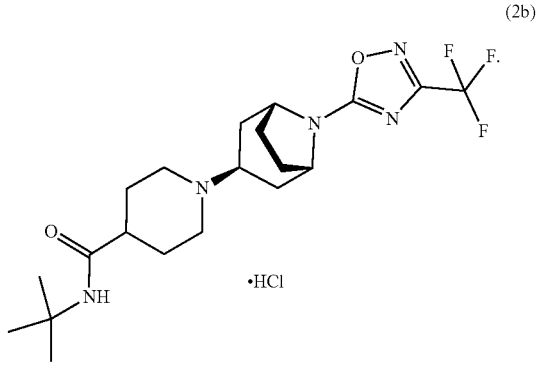

9. The compound according to claim 1, which is a compound of formula (2c):

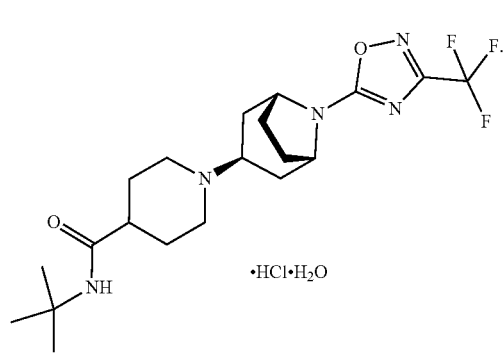

(2c)

·HCl·H₂O

10. A pharmaceutical composition comprising the compound according to claim 1, or a salt thereof, and a pharmaceutically acceptable excipient.

11. A method of treating a disorder selected from a cognitive disorder and a psychotic disorder in a subject, comprising administering to the subject the compound of claim 1, or a salt thereof.

12. The method according to claim 11, wherein the disorder is Alzheimer's disease.

13. The method according to claim 11, wherein the disorder is dementia with Lewy bodies.

14. The method according to claim 11, wherein the disorder is schizophrenia.

15. A salt of the compound according to claim 2.

16. A pharmaceutically acceptable salt of the compound according to claim 2.

17. An acid addition salt of the compound according to claim 2.

18. A hydrochloride salt of the compound according to claim 2.

19. A monohydrochloride salt of the compound according to claim 2.

20. A method of treating or lessening the severity of acute pain, chronic pain, neuropathic pain, or inflammatory pain in a subject, comprising administering to the subject the compound of claim 1, or a salt thereof.

21. A pharmaceutical composition comprising the compound according to claim 2, or a salt thereof, and a pharmaceutically acceptable excipient.

22. The method according to claim 11, which is a method of treating a cognitive disorder.

23. The method according to claim 22, wherein the cognitive disorder is a cognitive disorder associated with Alzheimer's disease.

24. A compound of formula (2):

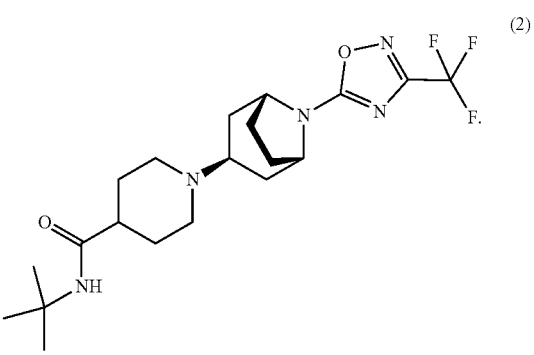

(2)

25. A pharmaceutical composition comprising the compound according to claim 24, and a pharmaceutically acceptable excipient.

26. A method of treating a disorder selected from a cognitive disorder and a psychotic disorder in a subject, comprising administering to the subject the compound according to claim 24.

27. The method according to claim 26, wherein the disorder is a cognitive disorder.

28. The method according to claim 27, wherein the cognitive disorder is a cognitive disorder associated with Alzheimer's disease.

29. The method according to claim 26, wherein the disorder is Alzheimer's disease.

30. The method according to claim 26, wherein the disorder is dementia with Lewy bodies.

31. The method according to claim 26, wherein the disorder is schizophrenia.

* * * * *

UNITED STATES PATENT AND TRADEMARK OFFICE
CERTIFICATE OF CORRECTION

PATENT NO. : 11,999,745 B2  
APPLICATION NO. : 17/874564  
DATED : June 4, 2024  
INVENTOR(S) : Charlotte Fieldhouse and Miles Stuart Congreve Page 1 of 4

It is certified that error appears in the above-identified patent and that said Letters Patent is hereby corrected as shown below:

On the Title Page

Column 2 item (56) (Other Publications), Line 5, delete "Ml" and insert -- M1 --.

Column 2 item (56) (Other Publications), Line 11, delete "tetrahydropyridy" and insert -- tetrahydropyridyl --.

Column 2 item (56) (Other Publications), Line 11, delete "5- thiadiazole" and insert -- 5-thiadiazole --.

Page 3, Column 1 item (56) (Other Publications), Line 13, delete "/condition s/" and insert -- /conditions/ --.

Page 3, Column 1 item (56) (Other Publications), Lines 40-41, delete "alzheimer- medications/>," and insert -- alzheimer-medications/>, --.

Page 3, Column 1 item (56) (Other Publications), Line 45, delete "Ml" and insert -- M1 --.

Page 3, Column 2 item (56) (Other Publications), Line 4, delete "acetylchloline" and insert -- acetylcholine --.

Page 3, Column 2 item (56) (Other Publications), Line 11, delete "action, "" and insert -- action," --.

Page 3, Column 2 item (56) (Other Publications), Line 16, delete "hMl" and insert -- hM1 --.

Page 3, Column 2 item (56) (Other Publications), Line 33, delete "Mi" and insert -- M1 --.

Page 3, Column 2 item (56) (Other Publications), Line 40, delete "ml-Selective" and insert -- m1-Selective --.

Signed and Sealed this  
First Day of April, 2025

Coke Morgan Stewart  
*Acting Director of the United States Patent and Trademark Office*

CERTIFICATE OF CORRECTION (continued)
U.S. Pat. No. 11,999,745 B2

Page 3, Column 2 item (56) (Other Publications), Line 41, delete "-1- Azabicyclo" and insert
-- -1-Azabicyclo --.

Page 3, Column 2 item (56) (Other Publications), Line 42, delete "-propynyl)- oxime" and insert
-- -propynyl)-oxime --.

Page 3, Column 2 item (56) (Other Publications), Line 43, delete "ml-Selective" and insert
-- m1-Selective --.

Page 3, Column 2 item (56) (Other Publications), Line 60, delete "17/024,085;" and insert
-- 16/450,261; --.

Page 3, Column 2 item (56) (Other Publications), Line 63, delete "18/133,036;" and insert
-- 16/450,279; --.

Page 3, Column 2 item (56) (Other Publications), Line 63, delete "18/133,036;" and insert
-- 17/069,070; --.

Page 3, Column 2 item (56) (Other Publications), Line 64, delete "18/133,036;" and insert
-- 17/708,494; --.

Page 3, Column 2 item (56) (Other Publications), Line 64, delete "18/133,036;" and insert
-- 17/958,599; --.

Page 3, Column 2 item (56) (Other Publications), Line 73, delete "3-(3-alkyl- 1,2,4-" and insert
-- 3-(3-alkyl-1,2,4- --.

Page 3, Column 2 item (56) (Other Publications), Line 73, delete "-y1)-" and insert -- -yl)- --.

Page 4, Column 1 item (56) (Other Publications), Line 1, delete "relationships, """ and insert
-- relationships," --.

Page 4, Column 1 item (56) (Other Publications), Line 4, delete "Chemitry," and insert
-- Chemistry, --.

In the Specification

Column 2, Line 14, delete "non-amyloidgenic" and insert -- non-amyloidogenic --.

Column 2, Line 14, delete "amyloidgenic." and insert -- amyloidogenic. --.

Column 2, Lines 18-19, delete "amyloidgenic" and insert -- amyloidogenic --.

Column 3, Line 2, delete "Neural)." and insert -- Neurol). --.

Column 8, Lines 58-59, delete "(–)-camphorsulphonic," and insert -- (–)-camphorsulfonic, --.

Column 11, Line 4, delete "/UCM5967 28.pdf)," and insert -- /UCM596728.pdf), --.

Column 15, Line 53, delete "978-O-470-" and insert -- 978-0-470- --.

Column 16, Line 18, delete "(e.g" and insert -- (e.g. --.

Column 17-18, Line 43, below "98:2 at 0.01 min" insert -- up to 0.50 min, --.

Column 17-18, Line 51, below "95:5 at 0.01 min," insert -- 10:90 at 5.00 min, --.

Column 19, Line 45, delete "((1R,3r5S)" and insert -- ((1R,3r,5S) --.

Column 24, Line 35, delete "((1R,3r5S)" and insert -- ((1R,3r,5S) --.

Column 24, Line 40, delete "-yl) azabicyclo" and insert -- -yl)-8-azabicyclo --.

Column 24, Line 48, delete "octan yl)" and insert -- octan-3-yl) --.

Column 24, Line 62, delete "((1R,3r5S)" and insert -- ((1R,3r,5S) --.

Column 24, Line 66, delete "((1R, 3r,5S)" and insert -- ((1R,3r,5S) --.

Column 25, Line 33, delete "((1R,3r5S)" and insert -- ((1R,3r,5S) --.

Column 25, Line 39, delete "piperidine carboxylate" and insert -- piperidine-4-carboxylate --.

Column 26, Line 1, delete "((1R,3r5S)" and insert -- ((1R,3r,5S) --.

Column 26, Line 7, delete "((1R,3r5S)" and insert -- ((1R,3r,5S) --.

Column 27, Line 15, delete "((1R,3r5S)" and insert -- ((1R,3r,5S) --.

Column 30, Line 9, delete "$_{16}$ h" and insert -- 16 h --.

Column 32, Line 63, delete "compound" and insert -- compound. --.

Column 33, Line 2, delete "13.1.01" and insert -- [3.1.0] --.

Column 33, Line 21, delete "cyclopent-3-ene carboxylate" and insert
-- cyclopent-3-ene-1-carboxylate --.

Column 34, Line 18, delete "-yl) azabicyclo" and insert -- -yl)-8-azabicyclo --.

CERTIFICATE OF CORRECTION (continued)
U.S. Pat. No. 11,999,745 B2

Column 35, Line 11, delete "piperidine carboxylate" and insert -- piperidine-4-carboxylate --.

Column 37, Line 2, delete "yl) azabicyclo" and insert -- yl)-8-azabicyclo --.

Column 38, Line 23, delete "yl)biperidine" and insert -- yl)piperidine --.

Column 39, Line 67, delete "483.96" and insert -- 483.96. --.

Column 41, Line 6, delete "pUmin/million" and insert -- µL/min/million --.

Column 41, Line 10, delete "incubation)" and insert -- incubation). --.

Column 41, Line 38, delete "DonorγIncubation" and insert -- Donor)/Incubation --.

Column 43, Line 50, delete "Kp,uu—ratio" and insert -- Kpuu—ratio --.

Column 44, Line 66, delete "dysfunction);" and insert -- dysfunction). --.